US010066029B2

(12) United States Patent
Grison et al.

(10) Patent No.: US 10,066,029 B2
(45) Date of Patent: Sep. 4, 2018

(54) USES OF CERTAIN PLATINOID ACCUMULATING PLANTS FOR USE IN ORGANIC CHEMICAL REACTIONS

(71) Applicants: CENTRE NATIONAL DE LA RECHERCHE SCIENTIFIQUE, Paris (FR); UNIVERSITE MONTPELLIER 2 SCIENCES ET TECHNIQUES, Montpellier (FR)

(72) Inventors: Claude Grison, Castelnau-le-Lez (FR); Vincent Escande, Montpellier (FR); Clemence Bes, Castelnau-le-Lez (FR); Brice-Loic Renard, Montpellier (FR)

(73) Assignees: CENTRE NATIONAL DE LA RECHERCHE SCIENTIFIQUE (C.N.R.S), Paris (FR); UNIVERSITE MONTPELLIER 2, SCIENCES ET TECHNIQUES, Montpellier (FR)

( * ) Notice: Subject to any disclaimer, the term of this patent is extended or adjusted under 35 U.S.C. 154(b) by 34 days.

(21) Appl. No.: 14/905,119

(22) PCT Filed: Jul. 15, 2014

(86) PCT No.: PCT/FR2014/051823
§ 371 (c)(1),
(2) Date: Jan. 14, 2016

(87) PCT Pub. No.: WO2015/007990
PCT Pub. Date: Jan. 22, 2015

(65) Prior Publication Data
US 2016/0159934 A1 Jun. 9, 2016

(30) Foreign Application Priority Data
Jul. 15, 2013 (FR) .................... 13 56964

(51) Int. Cl.
A61K 36/00 (2006.01)
C08B 37/08 (2006.01)
B01J 37/36 (2006.01)
B01J 23/40 (2006.01)
B09C 1/10 (2006.01)
C02F 3/32 (2006.01)
B01J 37/02 (2006.01)
B01J 37/06 (2006.01)
B01J 37/08 (2006.01)
B01J 37/16 (2006.01)
B01J 37/30 (2006.01)
B01J 23/42 (2006.01)
B01J 23/44 (2006.01)
B01J 23/46 (2006.01)
B01J 37/00 (2006.01)
C07B 37/04 (2006.01)
C22B 3/00 (2006.01)
C22B 3/18 (2006.01)
(Continued)

(52) U.S. Cl.
CPC ............ C08B 37/003 (2013.01); B01J 23/40 (2013.01); B01J 23/42 (2013.01); B01J 23/44 (2013.01); B01J 23/464 (2013.01); B01J 27/13 (2013.01); B01J 31/183 (2013.01); B01J 37/0036 (2013.01); B01J 37/0236 (2013.01); B01J 37/06 (2013.01); B01J 37/08 (2013.01); B01J 37/084 (2013.01); B01J 37/16 (2013.01); B01J 37/30 (2013.01); B01J 37/36 (2013.01); B09C 1/105 (2013.01); C02F 3/327 (2013.01); C07B 37/04 (2013.01); C07C 5/03 (2013.01); C07C 45/34 (2013.01); C07C 209/68 (2013.01); C07C 253/16 (2013.01); C07D 207/06 (2013.01); C22B 3/18 (2013.01); C22B 11/04 (2013.01); B01J 37/009 (2013.01); B01J 37/346 (2013.01); B01J 2231/4211 (2013.01); B01J 2231/4261 (2013.01); B01J 2231/52 (2013.01); B01J 2231/641 (2013.01); B01J 2231/70 (2013.01); B01J 2531/82 (2013.01); C02F 2101/10 (2013.01); C02F 2101/20 (2013.01); Y02P 10/234 (2015.11); Y02W 10/18 (2015.05)

(58) Field of Classification Search
CPC ....................................................... A61K 36/00
See application file for complete search history.

(56) References Cited

U.S. PATENT DOCUMENTS 4,525,218 A   6/1985   Chen et al.
9,149,796 B2  10/2015  Grison et al.
(Continued)

FOREIGN PATENT DOCUMENTS

CN   101381351   3/2009
EP   1 806 177   7/2007
(Continued)

OTHER PUBLICATIONS

Lustig et al, Platinum determination in nutrient plants by inductively coupled plasma mass spectrometry with special respect to the hafnium oxide interference. Fresenius' Journal of Analytical Chemistry (1997), vol. 357, No. 8, pp. 1157-1163.*
(Continued)

Primary Examiner — Qiuwen Mi
(74) Attorney, Agent, or Firm — Young & Thompson

(57) ABSTRACT

A composition derived from the acid treatment of ashes obtained after heat treatment of selected plants or plant material is provided. The selected plants accumulate metal from the platinum group (platinoids). The compositions can be used to produce catalysts for performing various organic synthesis reactions.

13 Claims, 2 Drawing Sheets

(51) Int. Cl.
| | | |
|---|---|---|
| *B01J 27/13* | (2006.01) | |
| *B01J 31/18* | (2006.01) | |
| *C07C 5/03* | (2006.01) | |
| *C07C 45/34* | (2006.01) | |
| *C07C 209/68* | (2006.01) | |
| *C07C 253/16* | (2006.01) | |
| *C07D 207/06* | (2006.01) | |
| *B01J 37/34* | (2006.01) | |
| *C02F 101/10* | (2006.01) | |
| *C02F 101/20* | (2006.01) | |

(56) References Cited

U.S. PATENT DOCUMENTS

| | | |
|---|---|---|
| 2005/0217174 A1 | 10/2005 | Angle et al. |
| 2008/0008676 A1 | 1/2008 | Janardanan Nair et al. |
| 2015/0011749 A1 | 1/2015 | Grison et al. |
| 2015/0174566 A1 | 6/2015 | Grison et al. |

FOREIGN PATENT DOCUMENTS

| | | |
|---|---|---|
| EP | 2 327 476 | 6/2011 |
| GB | 1 604 768 | 12/1981 |
| WO | 94-29226 | 12/1994 |
| WO | 97-34714 | 9/1997 |
| WO | 00-28093 | 5/2000 |
| WO | 2006-096472 | 9/2006 |
| WO | 2007-083304 | 7/2007 |
| WO | 2011-064462 | 6/2011 |
| WO | 2011-064487 | 6/2011 |
| WO | 2013-150197 | 10/2013 |
| WO | 2014-016509 | 1/2014 |
| WO | 2014-128283 | 8/2014 |
| WO | 2015-007990 | 1/2015 |

OTHER PUBLICATIONS

Hu et al., "Tolerance, accumulation and distribution of zinc and cadmium in hyperaccumulator Potentilla griththii," Environmental and Experimental Botany, vol. 66, pp. 317-325, 2009.

Kastner et al., "Low Temperature Catalytic Oxidation of Hydrogen Sulfide and Methanethiol Using Wood and Coal Fly Ash," Environ. Sci. Technol., vol. 37, pp. 2568-2574, 2003.

Kolar et al., "Low temperature catalytic oxidation of aldehydes using wood fly ash and molecular oxygen," Applied Catalysts B: Environmental, vol. 76, pp. 203-217, 2007.

Lievens et al., "Study of the potential valorisation of heavy metal contaminated biomass via phytoremediation by fast pyrolysis: Part I. Influence of temperature, biomass species and solid heat carrier on the behaviour of heavy metals," Fuel, vol. 87, pp. 1894-1905, 2008.

Losfeld et al., "Design and performance of supported Lewis acid catalysts derived from metal contaminated piomass for Friedel-Crafts alkylation and acylation," Catalysis Today, vol. 189, pp. 111-116, 2012.

Padmavathiamma et al., "Phytoremediation Technology: Hyper-accumulation Metals in Plants," Water Air Soil Pollut., vol. 184, pp. 105-126, 2007.

Ravindra et al., "Platinum group elements in the environment and their health risk," The Science of the Total Environment, vol. 318, pp. 1-43, 2004.

Stals et al., "Flash pyrolysis of heavy metal contaminated biomass from phytoremediation: Influence of temperature, entrained flow and wood/leaves blended pyrolysis on the behaviour of heavy metals," J. Anat. Appl. Pyrolysis, vol. 87, pp. 1-7, 2010.

Vamerali et al., "Field crops for phytoremediation of metal-contaminated land. A review," Environ. Chem. Lett., vol. 8, pp. 1-17, 2010.

Yang et al., "Heavy metal removal and crude bio-oil upgrade from Sedum alfredi Hance harvest using hydrothermal upgrading," Journal of Hazardous Materials, vol. 179, pp. 1037-1041, 2010.

Yang et al., "Heavy metal removal and crude bio-oil upgrading from Sedum plumbizincicola harvest using hydrothermal upgrading process," Bioresource Technology, vol. 101, pp. 7653-7657, 2010.

Zhang et al., "A newly found cadmium accumulator—Malva sinensis Cavan," Journal of Hazardous Materials, vol. 173, pp. 705-709, 2010.

* cited by examiner (a)

(b)

USES OF CERTAIN PLATINOID ACCUMULATING PLANTS FOR USE IN ORGANIC CHEMICAL REACTIONS

FIELD OF THE INVENTION

The invention relates to the use of plants that accumulate metals of the platinum group (platinoids) for the implementation of chemical reactions.

BACKGROUND OF THE INVENTION

The biological decontamination of soils polluted with metals, metalloids, industrial and agricultural organic waste and discharges or radio-isotopes as well as the treatment of effluents contaminated with metallic residues are problems of great concern as the soil performs essential functions which largely determine the production of food products and water quality.

Among the different polluting substances, heavy metals are among the most harmful compounds, as they are not biodegradable and become concentrated in the soils. Examples of sites exist in France, Belgium, Luxembourg, in the Jura, the Lower Swiss Alps or in the Pyrenees, to mention only the nearest regions as well as in more distant regions such as New Caledonia where nickel is more particularly exploited. Various African countries such as Gabon, Mali, South Africa, and also Mexico, China, India or Australia are also good examples.

Technologies for decontaminating soil are difficult to develop, as it is a heterogeneous, complex and dynamic medium, which plays a key role as a buffer and pollutant processor.

Different techniques of phytoremediation (phytoextraction, phytodegradation, phytostabilization, phytostimulation, phytotransformation, phytovolatilization and rhizofiltration) are currently being developed (Terry, N. and Banuelos G., editors, Phytoremediation of contaminated soil in water, Lewis Publishers, Boca Raton, Fla. 2000).

The CNRS is studying the technique of phytostabilization which consists of cultivating the contaminated soils with plants capable of growing in the presence of heavy metals (the term tolerance is used) (Frerot et al., Specific interactions between local metallicolous plants improve the phytostabilization of mine soils, Plant and Soil, 282, 53-65, 2006). Certain of these plant species used have the distinctive feature of accumulating large quantities of metals in their vacuoles (the term hyperaccumulating plants is used). Then it is a question of phytoextraction.

The team has quite particularly studied two plants; one of them, *Thlaspi caerulescens* (synonym *Noccaea caerulescens*) belonging to the Brassicaceae family, has remarkable properties of tolerance and hyperaccumulation of zinc, cadmium, nickel. It concentrates them in the aerial parts (leaves and stems).

This plant is capable of storing zinc at concentrations 100 times greater than that of a conventional plant. Moreover, it is capable of extracting and concentrating zinc and cadmium in the aerial tissues, even on soils having a low concentration of these two metals.

In addition to their unusual tolerance to $Zn^{2+}$ and $Cd^{2+}$ and to other metals, the hyperaccumulating plants are capable of extracting the metals and transferring them to the aerial parts where they are concentrated. Due to this fact, the roots have a very low heavy metal content, unlike non-accumulating plant species. This triple property of tolerance/accumulation/concentration in the parts which can be harvested is in fact a relevant tool in phytoremediation.

Moreover, heavy metals are commonly used in organic chemistry as catalysts that are indispensable to carrying out chemical conversions which require significant activation energy. The role of the catalysts is then to lower the energy barrier.

Their operating mode is frequently based on their Lewis acid properties. Zinc chloride is one of the most used and is indispensable in numerous industrial and laboratory reactions. It is also frequently used in heterocyclic organic chemistry for catalyzing numerous aromatic electrophilic substitutions.

It is also a catalyst of choice for carrying out hydrogenations of primary alcohols with Lucas' reagent, acetalization, aldolization reactions or cycloaddition reactions of the Diels-Alder type etc.

The catalysts are also very useful in analytical electrochemistry, electrometallurgy and liquid-solid extraction where the fields of application are numerous and directly involved in the different fields of economic life (batteries, fuel cells and accumulators, detectors of spectroscopic equipment, metallurgy, welding etc.)

In international application WO 2011/064462 and application WO 2011/064487 published on 3 Jun. 2011 the invention of Professor Grison and Doctor Escarré is described and claimed, which relates to the use of a calcined plant or a part of a calcined plant having accumulated at least one metal in the M(II) form chosen in particular from zinc (Zn), nickel (Ni) or copper (Cu), for the preparation of a composition containing at least one metal catalyst, the metal of which is one of the aforementioned metals in the M(II) form originating from said plant, said composition being devoid of chlorophyll, and allowing the implementation of organic synthesis reactions involving said catalyst.

In addition to the species mentioned above, *Thlaspi caerulescens* which is now called *Noccaea caerulescens* and *Anthyllis vulneraria*, application WO 2011/064487 describes the use of numerous other metallophyte plants which are hyperaccumulators of heavy metals for the preparation of catalysts which can be used in organic chemistry.

Therefore the invention described in WO 2011/064487 relates to the use of a calcined plant or part of a calcined plant having accumulated at least one metal in the M(II) form chosen in particular from zinc (Zn), nickel (Ni) or copper (Cu) as defined above, in which said plant is chosen in particular from the Brassicaceae family, in particular the species of the genus *Thlaspi* (synonym *Noccaea*) in particular *T. goesingense, T. tatrense, T. rotundifolium, T. praecox*, the species of the genus *Arabidopsis*, in particular *Arabidopsis hallerii*, and the genus *Alyssum*, in particular *A. bertolonii, A. serpyllifolium*, the Fabaceae, the Sapotaceae, in particular the species *Sebertia acuminata, Planchonella oxyedra*, the Convolvulaceae, in particular the species *Ipomea alpina*, the Rubiaceae, in particular the species *Psychotria douarrei*, in particular *P. costivenia, P. clementis, P. vanhermanii*, the Cunoniaceae, in particular the *Geissois*, the Scrophulariaceae, in particular the species of the genus *Bacopa*, in particular *Bacopa monnieri*, algae, in particular red algae, in particular the rhodophytes, more particularly *Rhodophyta bostrychia*, green algae or brown algae.

Due to this fact, the plant waste is directly recovered and converted to "green" catalysts or to unconventional reagents.

In French patent application No. 12/52045 filed on 6 Mar. 2012 and not yet published, Professor Grison and researchers Escande and Losfeld have unexpectedly shown that certain other plants which belong to the genus *Sedum* as well as a different plant, *Potentilla griffithii*, have metallophyte properties for hyperaccumulating different heavy metals which make them particularly interesting for use in organic chemistry catalysis.

The plants of the genus *Sedum* are succulents which belong to the Crassulaceae family, composed of more of 400 species. They have the natural aptitude to grow on poor, dry soils, in an open environment and under difficult conditions. Their foliar system is fleshy and they are easy to cultivate.

Among them, three species have developed unusual properties of extracting zinc and cadmium. *Sedum plumbizincicola* and *Sedum jinianum* have in particular a remarkable ability to extract zinc from the polluted soils of the south and east of China. They have real potential for phytoextraction and are described as "plumbizincicolafor".

However, the application of extracts of these plants as catalysts has never been described before and is the subject of French patent application No. 12/52045.

Professor Grison's team then discovered that the richness of the soil in mineral species such as manganese, can also be the basis for the progressive adaptation of plant communities, which become tolerant and hyperaccumulators of metallic trace elements, in particular Mn (II).

The following are examples of genera of plants comprising manganese hyperaccumulating species:
*Alyxia, Azolla, Beauprea, Beaupreopsis, Bridelia, Crotalaria, Dicranopteris, Dipteris, Eugenia, Garciania, Gleichenia, Gossia, Grevillea, Macadamia, Maytenus, Pinus, Spermacone, Stenocarpus, Virotia.*

These metallophyte species are thus capable of concentrating up to 110,000 ppm of manganese (as dry matter) in their foliar system. Their ability to grow on eroded mining sites, depleted of organic matter and exposed to dryness, makes these plants very useful for the ecological restoration of sites severely damaged by intensive mining operations.

The cultivation of such species, such as for example those of the genus *Grevillea*, has a use in addition to ecological restoration. They are the basis of new Lewis acid catalysts and high performance oxidizing reagents, the reactivity of which can be adjusted by controlling the degree of oxidation of the Mn and the composition of the medium. In the context of environmental crisis and tightening of European chemical regulations, the development of new mild, effective oxidizing systems which are environmentally sustainable is a real opportunity.

The treatments and preparations of the catalysts and oxidizing systems are easy, straightforward to implement and comply with green and ecological constraints.

The use of these plants is described and claimed in French application FR 12/57135, not yet published.

In European patent application No. EP 13 305 208, also not yet published, Professor Grison's team then discovered that certain plants chosen from *Psychotria douarrei, Geissois Pruinosa, Alyssum murale, Noccaea caerulescens* and *Anthyllis vulneraria* had the property of accumulating large quantities of Nickel (Ni) and could be used in preparing catalysts which can be used in organic chemistry.

Moreover, the chemistry of the platinoids represents a field essential for organic synthesis, that of reactions catalyzed by precious metals: platinum, palladium, osmium, iridium, ruthenium and rhodium. This field of chemistry is indispensable to the fine chemicals sectors: pharmacy, agrifood, agrochemistry, cosmetics and perfumery.

However, access to resources has become a key problem: they are mainly concentrated in a limited number of countries which are often politically unstable; worldwide resources worldwides are becoming depleted; ore extraction is contributing to the increase in energy costs. This general context is leading to a record increase in the cost of production.

Faced with such a situation, innovative recycling methods give the platinoids considerable significance.

The inventors of the applications mentioned above have shown that growing plants that accumulate metal cations on degraded mining sites, or in polluted aqueous environments, then recovering them for catalytic chemistry made it possible to resolve two major difficulties:

the bio-sourced catalysts make it possible to develop, heterogeneous catalysts that are very useful because they can be recovered by simple filtration and rinsing; they are therefore recyclable.

their performances are analogous to or better than those of their soluble homologues.

These results represent a true revolution in the field of catalytic chemistry. They also constitute a very attractive solution for overcoming the ecological and environmental problems of post-mining activities or treatment of industrial effluents.

SUMMARY OF THE INVENTION

The inventors of the present application have shown that it is possible to extend the whole method to the chemistry of the platinoids. The results open up new prospects in the field of chemical catalysis and green chemistry. The economic and strategic challenges are considerable. They are vital for the European economy.

Platinum (Pt), palladium (Pd) and rhodium (Rh) are 3 elements which form part of the group of the platinoids (PGEs). These are elements which are present in low quantities in the earth's crust, 0.005 $mg \cdot kg^{-1}$ in the case of Pt, 0.015 $mg \cdot kg^{-1}$ in the case of Pd and 0.0001 $mg \cdot kg^{-1}$ in the case of Rh, but the exploitation of which has not stopped increasing since the second half of the $20^{th}$ century. This increase is due in particular to their introduction into the catalytic converters of vehicles and to the demonstration of their exceptional properties as catalysts. Recycling still represents only a small part of the worldwide production of PGEs but given the current cost of their mining production this is an alternative route which would be worthwhile developing further.

On the other hand, with the increase in the worldwide production and consumption of PGEs, an increase has been observed in their emission into the environment (vehicle exhaust gases, industrial and hospital effluents) leading to PGE contamination at all levels, air, water and soil.

Therefore a first subject of the present application is the use after heat treatment of a plant or part of a plant belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial rye-grass (*Lolium perenne*), Italian rye-grass (*Lolium multillorum*), hooked bristlegrass (*Setaria verticillata*) and tobacco (*Nicotiana tabacum*) having accumulated at least one of the platinoids chosen from platinum, palladium, osmium, iridium, ruthenium, rhodium, preferably platinum (Pt), palladium (Pd) or rhodium (Rh) for the preparation of a composition containing at least one monoor polymetallic agent, the metal or metals of which are chosen from the metals originating from said plant, said composition being virtually depleted of organic matter, for the implementation of organic synthesis reactions involving said agent as catalyst.

A subject of the invention is also the use as catalyst, of a composition containing a metal catalyst originating after acid treatment of the ashes obtained after heat treatment of a plant or part of a plant belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial rye-grass (*Lolium perenne*), Italian rye-grass (*Lolium multillorum*), hooked bristlegrass (*Setaria verticillata*) and tobacco (*Nicotiana tabacum*), preferably white mustard (*Sinapis alba*), brown mustard (*Brassica juncea*), Italian rye-grass (*Lolium multiflorum*), having accumulated at least one of the platinoids chosen from platinum, palladium, osmium, iridium, ruthenium, rhodium, preferably platinum (Pt), palladium (Pd) or rhodium (Rh), a metal catalyst the metal or metals of which are chosen from the metals originating from said plant and the metal or metals of which present in the composition of the invention originate exclusively from the plant before calcination and preferably without the addition of metal coming from an origin other than said plant for the implementation of organic synthesis reactions involving said agent as catalyst.

A subject of the invention is also the use as described above characterized in that the heat treatment of a plant or part of a plant is carried out in air.

A subject of the invention is also the use as described above characterized in that the heat treatment of a plant or part of a plant is carried out under an inert gas atmosphere, preferably argon.

A subject of the invention is also the use of a composition prepared by heat treatment of a plant or part of a plant belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial rye-grass (*Lolium perenne*), Italian rye-grass (*Lolium multillorum*), hooked bristlegrass (*Setaria verticillata*) and tobacco (*Nicotiana tabacum*) having accumulated at least one of the platinoids chosen from platinum, palladium, osmium, iridium, ruthenium, rhodium, preferably platinum (Pt), palladium (Pd) or rhodium (Rh) and containing at least one mono- or polymetallic agent, the metal or metals of which are chosen from the metals originating from said plant, for the implementation of organic synthesis reactions involving said agent as catalyst.

A subject of the invention is also the use of a composition prepared by heat treatment in air of a plant or part of a plant belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial rye-grass (*Lolium perenne*), Italian rye-grass (*Lolium multillorum*), hooked bristlegrass (*Setaria verticillata*) and tobacco (*Nicotiana tabacum*) having accumulated at least one of the platinoids chosen from platinum, palladium, osmium, iridium, ruthenium, rhodium, preferably platinum (Pt), palladium (Pd) or rhodium (Rh) and containing at least one mono- or polymetallic agent, the metal or metals of which are chosen from the metals originating from said plant and the metal or metals of which present in the composition originate exclusively from the plant before heat treatment and without the addition of metal coming from an origin other than said plant, for the implementation of organic synthesis reactions involving said agent as catalyst.

A subject of the invention is also the use as described above, after heat treatment followed by an acid treatment, of a plant or part of a plant chosen from the genus chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial rye-grass (*Lolium perenne*), Italian rye-grass (*Lolium multiflorum*), hooked bristlegrass (*Setaria verticillata*) and tobacco (*Nicotiana tabacum*), having accumulated at least one of the platinoids chosen from platinum, palladium, osmium, iridium, ruthenium, rhodium, preferably platinum (Pt), palladium (Pd) or rhodium (Rh) characterized in that the acid treatment is preferably carried out with hydrochloric acid, in particular gaseous or aqueous HCl preferably at a concentration chosen between 1N and 12N, sulphuric acid, acetic acid, trifluoromethanesulphonic acid, nitric acid, perchloric acid, phosphoric acid, trifluoroacetic acid or para-toluene sulphonic acid, these acids preferably being used at a high concentration, preferably from 10 to 30%.

A subject of the invention is also the use as described above after heat treatment followed by an acid treatment of a plant or part of a plant chosen from the genus chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial rye-grass (*Lolium perenne*), Italian rye-grass (*Lolium multiflorum*), hooked bristlegrass (*Setaria verticillata*) and tobacco (*Nicotiana tabacum*), having accumulated at least one of the platinoids chosen from platinum, palladium, osmium, iridium, ruthenium, rhodium, preferably platinum (Pt), palladium (Pd) or rhodium (Rh) characterized in that the acid treatment is preferably carried out with hydrochloric acid, in particular gaseous HCl, 1N to 12N HCl, sulphuric acid, trifluoromethanesulphonic acid, nitric acid, perchloric acid, phosphoric acid, trifluoroacetic acid, para-toluene sulphonic acid, acetic acid, formic acid, oxalic acid or a mixture of acids such as the hydrochloric acid-nitric acid mixture or the acetic acid-nitric acid mixture preferably used at a high concentration, preferably from 10 to 30%.

The acid treatment of the ashes, obtained by heat treatment of the plants indicated above, can also be preceded by a treatment of these ashes with a salt or a mixture of several salts, preferably a mixture of sodium chloride and potassium disulphate, so as to obtain a molten mixture, a molten mixture that is then treated with an acid as indicated above.

The treatment of the ashes with a salt is preferably used when the use according to the present application is carried out with plants or parts of plants accumulating Rhodium.

A subject of the present invention is also a method for the preparation of a composition comprising a metallic or polymetallic agent comprising at least one of the platinoids chosen from platinum, palladium, osmium, iridium, ruthenium, rhodium, preferably platinum (Pt), palladium (Pd) or rhodium (Rh) characterized in that it comprises the following steps:

a) Dehydrating, preferably at ambient temperature or in an oven at a temperature of the order of 70° C., the biomass comprising the leaves, stems and/or roots of a plant or an extract from a plant belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial rye-grass (*Lolium perenne*), Italian rye-grass (*Lolium multiflorum*), hooked bristlegrass (*Setaria verticillata*) and tobacco (*Nicotiana tabacum*) having accumulated one of the platinoids chosen from platinum, palladium, osmium, iridium, ruthenium, rhodium, preferably platinum (Pt), palladium (Pd) or rhodium (Rh), and, if desired b) Grinding the dry biomass of a plant or an extract from a plant obtained in step a) optionally in the presence of a salt or a mixture of salts, preferably sodium chloride and potassium disulphate, c) Heat treatment in air or under an argon atmosphere of the biomass obtained in step a) or of the ground mixture obtained in step b) in an oven, preferably in one or more steps preferably in one step at 500-600° for several hours, preferably for approximately 2 hours or in two steps, the first at a temperature of less than 500° C. preferably of the order of 350° and the second step at a temperature of the order of 550° each of these steps being carried out for approximately 3 hours and, if desired, d) Treating the ashes obtained in step c) with a salt or a mixture of several salts preferably a mixture of sodium chloride and potassium disulphate so as to obtain a molten mixture after heating and, if desired, e) Treating the ashes obtained in step c) or of the molten mixture obtained in step d) by an acid solution, said acid being preferably chosen from hydrochloric acid preferably at a concentration chosen between 1M and 12 M or nitric acid, sulphuric acid, trifluoromethanesulphonic acid, nitric acid, formic acid, oxalic acid, perchloric acid, phosphoric acid, trifluoroacetic acid or para-toluene sulphonic acid, these acids preferably being used at a high concentration preferably from 10 to 30% treatment followed, if desired, by filtration preferably on celite and dehydration of the solution or suspension obtained preferably under reduced pressure so as to obtain a dry residue which can be dried at 120° C., and, if desired, f) Action on the product obtained in step c), d) or e) of acetic acid in the presence of a strong acid, preferably nitric acid, in order to obtain after concentration under reduced pressure, a solid which is then taken up in an organic solvent, preferably acetone or ethyl acetate in order to produce, after evaporation, a product in the form of acetate and, if desired, g) Reacting the product obtained in step e) containing rhodium with triphenylphosphine in order to obtain a pure complex of formula $RhCl(PPh_3)_3$ by precipitation and, if desired, h) Mixing or treating the product obtained in step c), d), e), f) or g) in an acid medium with a mineral support chosen from montmorillonite K10, silica, alumina, hydrotalcite, activated carbon or an organic support, preferably chitosan, in order to obtain after filtration, then drying in an oven or under vacuum, a catalyst supported on a mineral or organic support and, if desired, i) Partial purification of the dry residue obtained in step c), d), e), f), g) or h) on ion exchange resins followed, if desired, by dehydration of the solution obtained, preferably under reduced pressure so as to obtain a dry residue and, if desired, j) Reacting the product obtained in step c), d), e), f), g), h) or i) in dry form with ligands, preferably organic, under the optional action of micro-waves in order to obtain liganded agents.

In step d) of the method, the optional obtaining of a molten mixture among the ashes obtained in step c) and the acid salts is carried out preferably with plants or parts of plants accumulating Rhodium.

Therefore a particular subject of the present invention is a method characterized in that when steps a) to c) of the method are carried out with of the rhodium-accumulating plants the ashes obtained in step c) are treated with a salt or a mixture of several salts, preferably a mixture of sodium chloride and potassium disulphate so as to obtain a molten mixture.

DETAILED DESCRIPTION OF THE INVENTION

Figure 1:
FIGS. 1a and 1b are photographs of root hairs from *Lolium multiflorum*.
Figure 1:
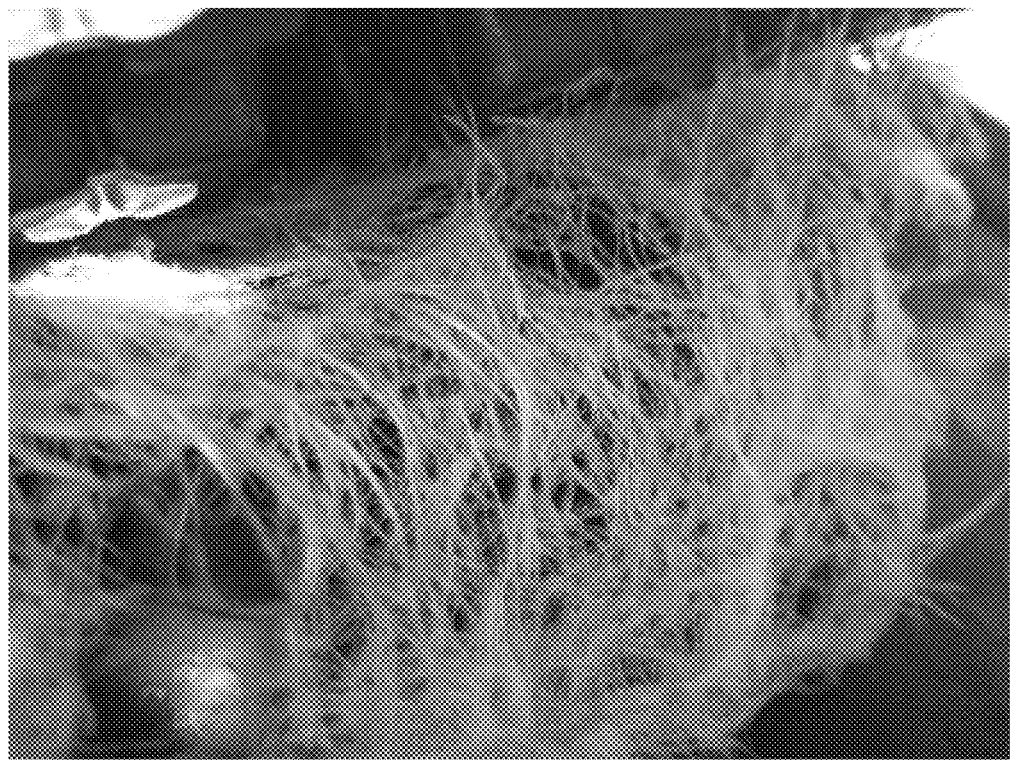

Preferentially and without it constituting a limitation to the present application, the catalysts derived from the platinoid-accumulating biomasss are prepared as follows:

1) Specific Preparation of the Catalysts with Palladium or with Platinum:

Treatment of Biomass: Catalysts of Type 1: Eco-$Pd_{cat1}$ and Eco-$Pd_{cat2}$

The collected leaves, stems or preferably the roots are dehydrated, either at ambient temperature, or in an oven (70° C.). The dry mass obtained is subjected to a heat treatment at 550° C. for 2 h in air (Eco-$Pd_{cat1}$) or under argon (Eco-$Pd_{cat2}$) in order to destroy the organic matter. The catalysts, Eco-$Pd_{cat1}$ and Eco-$Pd_{cat2}$, mixtures of polymetallic species and organic matter, are used directly or stored with a view to the following operations for the preparation of catalysts.

Acid Treatment of the Eco-Pd$_{cat1}$ and Eco-Pd$_{cat2}$ Originating from the Biomass: Catalyst of Type 2: Eco-Pd$_{cat3}$ and Eco-Pd$_{cat4}$ The Eco-Pd$_{cat1}$ and Eco-Pd$_{cat2}$ catalysts obtained after heat treatment of the biomass are introduced into an Erlenmeyer flask equipped with a magnetic stirrer, then an acid solution, which when hydrochloric acid is used can have a concentration comprised between 1 and 12 M, is introduced progressively, under stirring. Other acids such as nitric or sulphuric acid can be used at high concentrations preferably from 10 to 30%. Typically, 100 mL of acid solution is used for 10 g of Eco-Pd$_{cat1}$ or Eco-Pd$_{cat2}$. The resulting suspension is heated at reflux, under stirring, for 24 h. The mixture is then filtered on celite and the resulting solution is concentrated by evaporation under reduced pressure, until a catalytic solid is obtained. This is recovered, then it is dried in an oven (120° C.) until the solid mass stabilizes. This catalyst is then stored in a desiccator.

Modification of the Counter-Ion: Formation of the Acetate: Catalyst of Type 3: Eco-Pd$_{cat5}$ and Eco-Pd$_{cat6}$ It is possible to carry out a counter-ion exchange starting from Eco-Pd$_{cat3}$ or Eco-Pd$_{cat4}$ obtained following the preceding treatment, in particular in order to form a catalyst in the form of acetate, which is more soluble in organic solvents. Typically, 100 mg of Eco-Pd$_{cat3}$ is introduced into a flask equipped with a magnetic stirrer then 10 mL of acetic acid at 95% and 60 µL of nitric acid (65%) are added. The solution obtained is stirred, at reflux, for 3 hours. This is then concentrated under reduced pressure, until an orange solid is obtained. This solid is taken up in a solvent such as acetone or ethyl acetate. The evaporation of this organic phase leads to the catalyst being obtained in the acetate form.

Catalyst Supported on a Mineral Support: Catalyst of Type 4

Different mineral supports can be used for supporting the catalyst and thus producing catalysis on a support. Typically, montmorillonite K10, silica, alumina or hydrotalcite have been used as a support. 1 g of mineral support is introduced into a flask equipped with a magnetic stirrer, then 50 mg of catalyst of type 2 or 3 is added. 10 mL of water is added, then the resulting suspension is stirred at ambient temperature for 5 h. This is then filtered, the solid is washed with 5×10 mL of distilled water, then this is collected for drying in an oven (120° C.) overnight. Once its mass has stabilized, the resulting catalyst is stored in a desiccator.

Catalyst Supported on an Organic Support: Catalyst of Type 5

The catalyst can also be supported on organic solids, in particular of natural origin, such as chitosan derivatives. This involves the preparation of an organic support starting from chitosan according to the following procedure: 15 mL of methanol, 1 g of chitosan, 1.6 g (15 mmol) of 2-pyridinecarboxaldehyde, 1.5 mL (26 mmol) of concentrated acetic acid are introduced into a flask equipped with a magnetic stirrer. The mixture is heated at reflux, under stirring, for 10 h, under a dinitrogen stream. The mixture is then filtered, the residual solid is washed with water (25 mL), ethanol (25 mL) then acetone (25 mL), then dried under vacuum for 3 h at 60° C. This solid is then used as a support for a catalyst prepared according to the following procedure: 100 mg of organic support prepared above, 10 mg of catalyst of type 2 and 10 mL of acetone are introduced into a flask equipped with a magnetic stirrer. The mixture is stirred at ambient temperature for 48 h then filtered, washed with water (25 mL), ethanol (25 mL) then acetone (25 mL), then dried under vacuum for 3 h at 60° C.

Catalyst Treated with an Organic Reducing Acid, Formic or Oxalic Acid: Catalyst of Type 6: Eco-Pd$_{cat7}$ and Eco-Pd$_{cat8}$ 5 g of Eco-Pd$_{cat1}$ or Eco-Pd$_{cat2}$ obtained by heat treatment at 400° C. of the corresponding roots, are dispersed in 150 mL of formic acid. The solution is stirred at 90° C. The solution darkens quite rapidly. After stirring for 30 h, the reaction mixture is filtered on celite. A pale yellow solution and a black residual solid are isolated and put aside. The solid residue which is partly composed of palladium (0) is washed with boiling water. 3.210 g of a black solid is analyzed by ICP MS. It is 9.1% composed of Pd.

Catalyst Liganded with Cyclooctadiene: Catalyst of Type 7:

10 mg of Eco-Pd$_{cat3}$ and 200 µl of 37% HCl are introduced into a 5 mL flask. When a pale yellow suspension appears, 2 mL of ethanol and 60 µl of cyclooctadiene are added. After concentration under nitrogen and washing with 3×2 mL of ethyl acetate and drying over sodium sulphate, the medium is concentrated under vacuum. 5.6 mL of a bright yellow oil is stored in 10 mL of acetone. ICP MS analysis indicates 463 ppm of Pd.

Catalyst Treated with a Mixture of Hydrochloric Acid, Nitric Acid and Activated Carbon Before Reduction: Catalyst of Type 8: Eco-Pd$_{cat8}$ and Eco-Pd$_{cat9}$ Typically, 10 g of catalysts of type 2 are solubilized in 20 ml of concentrated hydrochloric acid and 50 mL of water. The solution is diluted with 100 mL of water, then poured into 90 g of carbon previously activated with a 10% nitric acid solution for 2 hours, washed, filtered and dried in an oven at 100° C. The mixture is stirred, dried with a water bath then in an oven at 100° C. The solid (approximately 100 g) is placed in a desiccator under vacuum in the presence of calcium chloride. The Pd(II) of the polymetallic catalyst can be reduced to Pd(0) by dihydrogen, hydrazine, sodium borohydride, formaldehyde, but research into green conditions rather suggests the use of formic acid or one of these salts, or oxalic acid.

2) Specific Preparation of the Rhodium Catalyst:

The oxides obtained after heat treatment of the biomass are ground in a mortar with a mixture of sodium chloride and potassium disulphate. The mixture is placed in a pyrex crystallising dish or a porcelain crucible then heated in an oven at 500-600° C. for 2 hours. After cooling, the finely ground reddish solid is introduced into an aqueous solution of concentrated hydrochloric acid and stirred for 1 hour at reflux. The resulting solution is concentrated by evaporation under reduced pressure, until a catalytic solid is obtained. This is recovered, then it is dried in an oven (120° C.) until the solid mass stabilizes. This catalyst is then stored in a desiccator.

Certain reactions require a biosourced rhodium catalyst of high purity. In the case of catalytic hydrogenations, a catalyst of high purity can be prepared by precipitation of the RhCl(PPh$_3$)$_3$ complex. An example of such a preparation is given hereafter in the experimental section. In the case of reactions that do not require the RhCl(PPh$_3$)$_3$ complex, a catalyst of high purity can be obtained by purification on ion exchange resins.

The ion exchange technique is widely used for the recycling and separation of rhodium from the other platinoids, transition metals and alkali metals. The rhodium complexes can be purified for example on cation exchange resins such as Wofatit KPS-200 or Vionit CS-3.

A subject of the invention is also a method characterized in that the plants belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial rye-grass (*Lolium perenne*), Italian rye-grass (*Lolium multiflorum*), hooked bristlegrass (*Setaria verticillata*) and tobacco (*Nicotiana tabacum*) are cultivated in the presence of effluents contaminated with one of the platinoids chosen from platinum, palladium, osmium, iridium, ruthenium, rhodium, preferably platinum (Pt), palladium (Pd) or rhodium (Rh), so as to accumulate said metals in the leaves, stems and/or roots.

The preferred operating method consists of using the PGE-contaminated effluents, preferably by subjecting these effluents to an acidification treatment in order to lower the pH to a range comprised between pH 3 and pH 6 in order to increase the solubility of the PGEs and the availability of the PGEs for the plants and then cultivating the potentially hyperaccumulating plants in contact with these effluents.

Therefore a subject of the invention is a method characterized in that the effluents contaminated with one of the platinoids chosen from platinum, palladium, osmium, iridium, ruthenium, rhodium, preferably platinum (Pt), palladium (Pd) or rhodium (Rh) are treated with an acid preferably chosen from hydrochloric acid, nitric acid, sulphuric acid, trifluoromethanesulphonic acid, nitric acid, perchloric acid, phosphoric acid or an organic acid such as acetic acid, citric acid, malic acid, lactic acid so as to obtain a solution, the pH of which is preferably comprised between 3 and 6, before being placed in contact with the platinoid-accumulating plants.

A subject of the invention is also a method characterized in that the effluents contaminated with one of the platinoids chosen from platinum, palladium, osmium, iridium, ruthenium, rhodium, preferably platinum (Pt), palladium (Pd) or rhodium (Rh) are treated with an acid preferably chosen from hydrochloric acid, nitric acid, sulphuric acid, trifluoromethanesulphonic acid, nitric acid, perchloric acid, or phosphoric acid, preferably nitric acid used alone, so as to obtain a solution, the pH of which is preferably comprised between 2 and 6, before being placed in contact with the platinoid-accumulating plants.

It may be preferable to carry out a neutralization with ammonia when nitric acid is used by itself.

As regards cultivation of the platinoid-accumulating plants, two cultivation methods are possible, 1) using the effluents for watering the plants cultivated in an uncontaminated medium (sand for example) or 2) cultivating the plants hydroponically directly in the contaminated medium (effluents).

Numerous species are capable of collecting the PGEs and some are capable of concentrating them in their roots at a very high concentration when they are cultivated in these ways.

Therefore a subject of the invention is a method characterized in that the crops of plants belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial rye-grass (*Lolium perenne*), Italian rye-grass (*Lolium multiflorum*), hooked bristlegrass (*Setaria verticillata*) and tobacco (*Nicotiana tabacum*) are cultivated in a sterile medium watered with the effluents contaminated with at least one of the platinoids chosen from platinum, palladium, osmium, iridium, ruthenium, rhodium, preferably platinum (Pt), palladium (Pd) or rhodium (Rh) or are cultivated hydroponically or aeroponically in the contaminated effluents Preferentially and without it constituting a limitation to the present application, the platinoid-accumulating plants are cultivated as follows:

1) Cultivation on Uncontaminated Sand:

The species are germinated in pots containing sterile sand and placed in large trays containing the growing solution, starting with water and fertilizer. Then after growing for 2 weeks, the growing solution is replaced with a new solution constituted by the effluents which have been previously heat-treated then taken up in $HNO_3$ (and optionally neutralization with ammonia) and fertilizer. After being exposed for 4 weeks, the roots and aerial parts of the plants are collected, washed, dried and weighed. Then the samples are burnt in a muffle furnace at 350° C. for 3 hours then at 550° C. for 3 hours. The ashes are then used for the preparation of the catalysts. This method is optimum for plants that cannot be grown hydroponically and are less tolerant of an excess of PGE. High concentrations are reached in the roots.

| Common name | Latin name | Type | Cultivation | Concentration reached in the roots | Concentration reached in the catalysts |
|---|---|---|---|---|---|
| Brown mustard | *Brassica juncea* | Terrestrial | Sand | Pt: 57 mg · kg$^{-1}$<br>Pd: 5473 mg · kg$^{-1}$<br>Rh: 189 mg · kg$^{-1}$ | Pt: 671 mg · kg$^{-1}$<br>Pd: 12402 mg · kg$^{-1}$<br>Rh: 450 mg · kg$^{-1}$ |
| White mustard | *Sinapis alba* | Terrestrial | Sand | Pt: 101 mg · kg$^{-1}$<br>Pd: 6848 mg · kg$^{-1}$<br>Rh: 35 mg · kg$^{-1}$ | Pt: 1603 mg · kg$^{-1}$<br>Pd: 9418 mg · kg$^{-1}$<br>Rh: 35 mg · kg$^{-1}$ |
| Italian ryegrass | *Lolium multiflorum* | Terrestrial | Sand | Pt: 112 mg · kg$^{-1}$<br>Pd: 1100 mg · kg$^{-1}$<br>Rh: 64 mg · kg$^{-1}$ | Pt: 1207 mg · kg$^{-1}$<br>Pd: 5111 mg · kg$^{-1}$<br>Rh: 633 mg · kg$^{-1}$ |

2) Hydroponic Cultivation Intended for the Rhizofiltration of Effluents

The species are germinated in "Fleximix Root Riot Organic Starter Cubes" coconut tubes. This substrate is constituted by coconut coir, peat and coconut shells. The seeds of each species are then collected together on seeding trays and watered daily so as to avoid drying out.

For 15 days, the seedlings are arranged under neon lights, under a light intensity of 11,000 lumens. Monitoring the germination rate of the 260 seeds of 3 species, *Brassica juncea, Lolium multiflorum* and *Sinapsis alba*, shows values which are particularly interesting in the case of *Brassica juncea*, and above all *Lolium multiflorum*. The optimum value is around 12 to 13 days. The germination rates are the following:

*Brassica juncea:* 78.5%; *Lolium multiflorum:* 84.6%; *Sinapis alba:* 48%

A protocol of growth through one of the clay beads placed in mesh pots, arranged in turn on clay beads arranged on the bottom of the cultivation tray makes it possible to optimize root growth. In this way the clay beads make it possible to distance the roots from the nutrient solution and to promote the growth of the primary root. The fertilizer introduced into the nutrient solution must be introduced at low concentrations so as not to burn the young roots.

The plants are then transplanted and placed under mercury lamps which make it possible to provide a light intensity of 37,000 lumens. This lighting system promotes the development of the plant placed in a hydroponic system, but also the evapotranspiration of the plant species, which drives root absorption. Development of the average length of the longest root over time shows rapid and continuous growth of the initial primary root in the case of *Lolium*.

After exposure for 2 weeks the roots and aerial parts of the plants are collected, washed, dried and weighed. The effluent is analyzed each week in order to monitor the efficiency of the purification. The weekly bioaccumulation factor is evaluated. After 8 days, the effluent is 82% purified with *Brassica juncea*. However, the rapid flowering of the brassicaceae limits prolonged treatment due to rapid flowering, making complete extraction difficult. A species such as *Lolium mutiflorum* does not pose this problem. Its extraction is less spectacular, but this is largely compensated for by its root surface and its biological rhythm which are more in line with the objectives. Its performances are illustrated by the bioaccumulation in the roots presented hereafter, but also by the abundance of root biomass which corresponds perfectly to the objectives of recovery by chemical catalysis.

The samples are then burnt in a muffle furnace at 350° C. for 3 hours then at 550° C. for 3 hours. The heat treatment is carried out either in air, or under argon. Then the ashes are used for the preparation of the catalysts. This method is optimum as it allows a large biomass to be obtained rapidly and allows better accumulation in the roots; it is ideal for aquatic plants and/or plants that are tolerant to an excess of PGE.

There is no translocation phenomenon observed in the three examples below, this is why only the data concerning the roots are presented.

| Common name | Latin name | Type | Cultivation | Concentration reached in the roots | Concentration reached in the catalysts |
|---|---|---|---|---|---|
| Brown mustard | *Brassica juncea* | Terrestrial | Hydroponics | Pt: 1938 mg · kg$^{-1}$ Pd: 21150 mg · kg$^{-1}$ Rh: 1512 mg · kg$^{-1}$ | Pt: 17442 mg · kg$^{-1}$ Pd: 126900 mg · kg$^{-1}$ Rh: 10584 mg · kg$^{-1}$ |
| Italian ryegrass | *Lolium multiflorum* | Terrestrial | Hydroponics | Pt: 3781 mg · kg$^{-1}$ Pd: 4400 mg · kg$^{-1}$ Rh: 509 mg · kg$^{-1}$ | Pt: 52934 mg · kg$^{-1}$ Pd: 62800 mg · kg$^{-1}$ Rh: 4581 mg · kg$^{-1}$ |
| White mustard | *Sinapis alba* | Terrestrial | Hydroponics | Pt: 3434 mg · kg$^{-1}$ Pd: 27392 mg · kg$^{-1}$ Rh: 280 mg · kg$^{-1}$ | Pt: 106454 mg · kg$^{-1}$ Pd: 164352 mg · kg$^{-1}$ Rh: 19320 mg · kg$^{-1}$ |

Inter-species comparison of the size of the biggest root at 40 days produces the following results:

*Brassica juncea:* 40 cm; *Lolium multiflorum:* 8 cm; *Sinapis alba:* 8 cm

Adventitious roots appear rapidly on the root initially measured, in the case of *Lolium multiflorum*. The roots rapidly form root hairs ideal for extraction of the metals present in the effluents to be purified (FIGS. 1 (*a*) and (*b*)).

Figure 2:
FIG. 2 is a photograph of pots suspended through a polystyrene tray.

The accumulation experiments are carried out hydroponically or aeroponically. It is recommended not to use a substrate such as fine sand or clay beads, but to favour direct exposure of the roots to the effluent, in order to avoid absorption of the metals in the effluent by the substrate. Suspending the pots through a polystyrene tray is a simple solution (FIG. 2).

The effluent is an aqueous solution the metallic species of which originate from organic reactions, such as coupling reactions such as the Suzuki reaction. The salts have been previously heat-treated, then treated with HNO$_3$ (and optionally neutralization with ammonia). Thus, in the case of a Suzuki reaction, the solution to be reprocessed is rich in palladium nitrate or a salt derivative such as palladium ammonium nitrate. An ideal concentration is close to 40 mg/L and the pH must be maintained at 3, in order to avoid precipitation of the salts. The pH must be adjusted according to the type of each salt.

Therefore a subject of the invention is a cultivation method for the plants belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy phacelia (*Phacelia tanacetifolia*), radish (*Raphanus sativus*), perennial ryegrass (*Lolium perenne*), Italian rye-grass (*Lolium multiflorum*), hooked bristlegrass (*Setaria verticillata*) and tobacco (*Nicotiana tabacum*) in a sterile medium watered with the effluents contaminated with at least one of the platinoids chosen from platinum, palladium, osmium, iridium, ruthenium, rhodium, preferably platinum (Pt), palladium (Pd) or rhodium (Rh) characterized in that said plants are cultivated on uncontaminated sand for approximately 2 weeks in the presence of a growing solution mainly constituted by water and fertilizer then for approximately 2 weeks in the presence of a growing solution mainly constituted by the effluents and fertilizer.

Therefore a subject of the invention is a cultivation method for the plants belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy *phacelia* (*Phacelia tanacetifolia*), radish (*Raphanus sativus*), perennial ryegrass (*Lolium perenne*), Italian rye-grass (*Lolium multiflorum*), hooked bristlegrass (*Setaria verticillata*) and tobacco (*Nicotiana tabacum*) in a sterile medium watered with the effluents contaminated with at least one of the platinoids chosen from platinum, palladium, osmium, iridium, ruthenium, rhodium, preferably platinum (Pt), palladium (Pd) or rhodium (Rh) characterized in that said plants are cultivated hydroponically for approximately 2 weeks in the presence of a growing solution mainly constituted by water and fertilizer then for approximately 1 week in the presence of a growing solution mainly constituted by the effluents.

A particular subject of the invention is a cultivation method for the plants belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy *phacelia* (*Phacelia tanacetifolia*), radish (*Raphanus sativus*), perennial ryegrass (*Lolium perenne*), Italian rye-grass (*Lolium multiflorum*), hooked bristlegrass (*Setaria verticillata*) and tobacco (*Nicotiana tabacum*) characterized in that the concentration of the metals in the roots of the plants is comprised between 40 and 8,000 $mg \cdot kg^{-1}$ in the case of platinum, between 1,100 and 32,000 $mg \cdot kg^{-1}$ in the case of palladium and between 30 and 1,900 $mg \cdot kg^{-1}$ in the case of rhodium.

A subject of the invention is also a treatment method for the effluents contaminated with PGE in order to remediate the contaminated media while providing an alternative source of PGE which is useful for the purposes of catalysis for the green chemicals industry.

A subject of the invention is also a method as described above characterized in that the aqueous phase of the reaction mixture obtained after use as catalyst, of the compositions containing a metal catalyst originating, after acid treatment, from the ashes obtained after heat treatment of a plant or part of a plant as described above is recycled by rhizofiltration using said plants.

Therefore a subject of the invention is a method for decontaminating effluents contaminated with at least one of the platinoids chosen from platinum, palladium, osmium, iridium, ruthenium and rhodium characterized in that the plants capable of accumulating at least one of the platinoids belonging to one of the genera chosen from green arrow arum (*Peltandra virginica*), cucumber (*Cucumis sativus*), garden cress (*Lepidium sativum*), Canadian pondweed (*Elodea canadensis*), spinach (*Spinacia oleracea*), water hyacinth (*Eicchornia crassipes*), alfalfa (*Medicago sativa*), maize (*Zea mays*), white mustard (*Sinapis alba*), brown mustard (*Brassica juncea*), barley (*Hordeum vulgare*), nettle (*Urtica dioica*), lacy *phacelia* (*Phacelia tanacetifolia*), radish (*Raphanus sativus*), perennial rye-grass (*Lolium perenne*), Italian rye-grass (*Lolium multiflorum*), hooked bristlegrass (*Setaria verticillata*) and tobacco (*Nicotiana tabacum*) are cultivated in a medium watered by the contaminated effluents or hydroponically in the contaminated effluents.

The overall operating method is the same as that indicated above, it consists of recovering effluents contaminated with PGEs, treating these effluents in order to increase the solubility of the PGEs and then cultivating the potentially hyperaccumulating plants in contact with these effluents. Two methods are possible, 1) using the effluents to water the plants grown in an uncontaminated medium (sand for example) or 2) growing the plants hydroponically directly in the contaminated medium (effluents). Numerous species are capable of collecting the PGEs and some are capable of concentrating them in their roots at a very high concentration.

A subject of the present invention is also the use in which the composition containing at least one metallic or preferably polymetallic catalyst as described above is used in the implementation of organic synthesis reactions of functional conversions by catalysis chosen from the carbon-carbon bond formation reactions chosen from the Suzuki reaction, the Heck reaction, the Sonogashira reaction, the arylic coupling reactions chosen from the Kumada reaction, the Negishi and Fukuyama reaction, the Hiyama reaction, and the Stille reaction; the nucleophilic addition reactions of an enamine on the pi-allylic complexes, reactions of the Buchwald-Hartwig type, the carbonylation reactions and ene-reactions, the Wacker-Tsuji oxidation, the oxidation of alcohols, the oxidizing coupling of aromatic compounds, the regioselective reactions between an alkene and an aromatic derivative, the cyclopropanation of alkenes, the reduction of olefins and nitrated compounds, the hydrosilylation of olefins and alkynes, cycloadditions, the cascade carbocylization of polyunsaturated compounds, catalytic hydrogenation, allylic isomerization, cycloaddition, the ene-reactions, cycloisomerizations, and hydroboration.

A subject of the present invention is also the use of a composition containing at least one metallic or preferably polymetallic catalyst as described above for the implementation of the organic synthesis reactions of functional conversions by catalysis chosen from the carbon-carbon bond formation reactions such as the Suzuki reaction, the Heck reaction, the Sonogashira reaction; the nucleophilic addition reactions of an enamine on the pi-allylic complexes, reactions of the Buchwald-Hartwig type, the carbonylation reactions and ene-reactions, the Wacker-Tsuji oxidation, the oxidation of alcohols, the reduction of olefins and nitrated and nitrile compounds, the hydrosilylation of olefins and alkynes, allylic isomerization.

A more particular subject of the present invention is the use as described above in which the reaction is chosen from the Suzuki reaction, the Heck reaction, the Sonogashira reaction, and the reduction of olefins and of nitrated and nitrile compounds.

A more particular subject of the present invention is the use as described above in which the reaction is chosen from the formation of carbon-carbon bonds via the Heck reaction, the Suzuki reaction, green reductions.

A more particular subject of the present invention is the use as described above characterized in that the metallic or preferably polymetallic catalyst, preferably the palladium contained in the composition as described in one of these claims for the implementation of the organic synthesis reactions of functional conversions by catalysis preferably chosen from the Suzuki reaction, the Heck reaction, the Sonogashira reaction, and the reduction of olefins and of nitrated compounds, is used in very low doses, for example of the order of at least 0.001 mol % to 0.15 mol %, preferably of the order of at least 0.0025 mol % of Pd.

A more particular subject of the present invention is the use as described above characterized in that, in the composition containing at least one mono- or polymetallic agent used in the implementation of the organic synthesis reactions of functional conversions by catalysis, the concentration of metal is comprised between 600 and 120,000 mg·kg$^{-1}$ in the case of platinum, between 5,000 and 180,000 mg·kg$^{-1}$ in the case of palladium and between 30 and 22,000 mg·kg$^{-1}$ in the case of rhodium.

This use of the compositions containing at least one metallic or preferably polymetallic catalyst as described above in the implementation of the organic synthesis reactions of functional conversions by catalysis is preferably carried out under the following conditions:

Bio-Sourced Palladium Chemistry

I—Pd(0) Chemistry

One of the advantages of the biosourced catalysts which are the subject of the present application is their ability to catalyze the formation of carbon-carbon bonds with very low quantities of catalysts. This aspect is fundamental, given the particularly high cost of the PGEs. This aspect is illustrated in a detailed fashion with the carbopalladation reactions of Heck type and coupling reactions such as the Suzuki reaction.

1) Reaction of Aryl Halides with Alkenes or Aromatics (Heck Reaction)

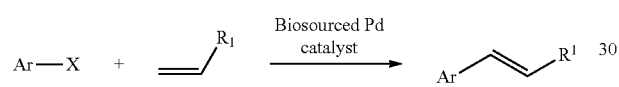

X=I, Br, Cl, $N_2^+$

Ar=carbocyclic or heterocyclic, mono- or polycyclic aromatic radical preferably a phenyl or a naphthyl.

The aryl can be mono- or disubstituted.

The reaction can also be carried out by replacing the Ar group with a vinyl group $R_1$=aromatic, COOR, CHO, C(O)R, CN, P(O)(OR)$_2$ group in which R represents an alkyl radical having 1 to 6 carbon atoms.

The nature of the Eco-Pd catalyst which can be used varies:

The catalysts of type 1, 2, 3, 4, 5 and 6.

From a general point of view, the catalytic activities increase in the following way: catalysts of type 3>catalysts of type 2>catalysts of type 4>catalysts of type 1>catalysts of type 5.

Different bases have been tested: triethylamine, often recommended in conventional Heck reactions, alkaline carbonates and sodium acetate. In this case it is the weaker and greener base, AcONa, that is the most effective.

The presence or absence of water are not determining factors. On the other hand, it is important to work under an inert atmosphere. Nitrogen is sufficient.

The addition of diode conventionally recommended for limiting the formation of agglomerates of Pd (0) is of no use. On the other hand, the presence of tetrabutylammonium bromide improves yields appreciably (20% on average).

The addition of phosphine ligands is of no use. The present method does not require organic ligands, palladium being easily reduced in situ by the species present in the reaction medium as described in (a) Beletskaya, I. P.; Cheprakov, A. V., The Heck Reaction as a Sharpening Stone of Palladium Catalysis. *Chemical Reviews* 2000, 100 (8), 3009-3066; (b) Ziegler, C. B.; Heck, R. F., Palladium-catalyzed vinylic substitution with highly activated aryl halides. *The Journal of Organic Chemistry* 1978, 43 (15), 2941-2946. It is an appreciable advantage given their cost and chemical or thermal instability. The absence of phosphine ligands also reflects the good stability of the bio-sourced catalytic systems.

A few examples which are typical and carried out with the catalyst of type 3 system (1.17×10$^{-4}$ mmol of Pd)/TBAB (6×10$^{-2}$ mmol)/AcONa (0.13 mmole/ArX (0.10 mmole)/olefin (0.16 mmole)/under nitrogen/24 h/140° C. are shown in the following table:

| ArX | $R_1$ ⇌ | Ar ⇌ $R^1$ Yield % |
|---|---|---|
| I-phenyl | styrene | 87 |
| I-phenyl | ⇌COOMe | 100 |
| 4-CN-Br-phenyl | ⇌COOMe | 100 |
| 4-MeO-I-phenyl | styrene | 55 |
| 4-acetyl-Br-phenyl | styrene | 98 |
| Br-phenyl | styrene | 86 |
| I-naphthyl | 2-CN-thiophene | 81 |

Given the current geoeconomic context, the most important factor is the minimal quantity of palladium necessary for the reaction. Conventional systems use quantities of the order of 2-5 mol % (Chem Rev. 2000, 100, 3009-3066; Tetrahedron lett. 1998, 39, 8449-8452). Optimized systems have been able to reduce the quantities of Pd to 1-1.5 mol %. In a typical method, M. Retz et al. (Tetrahedron lett. 1998, 39, 8449-8452) describe an experimental method with 1.5 mol % and raises the possibility of reducing the quantity to 0.0009 mol % under specific conditions. Other authors propose catalytic systems using 0.01 mol % (J. Am. Chem. Soc. 2001, 123, 5990-5999; 0.05% (Org. Lett. 2003, 5, 3285-3288) and 0.004% (J. Mol. Cat. A. 2009, 154, 39-44).

The results presented are therefore particularly favourable, as they describe a general method using 0.07 mol % of Pd. Combined with the possibility of ecological recycling, the method described is therefore particularly interesting both from a chemical and an ecological point of view.

2) Arylic Coupling Reaction with Organometallic Compounds (Mg: Kumada, Zn: Negishi and Fukuyama, Si: Hiyama, B: Suzuki, Sn: Stille)

This mechanism is illustrated with the Suzuki reaction:

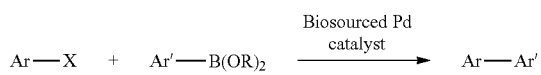

Ar, Ar'=aromatic radical R=H, alkyl, aryl X=I, Br, Cl, OS(O)$_2$R

Ar and Ar' represent a mono- or disubstituted, mono- or polycyclic, carbocyclic or heterocyclic, aromatic radical, preferably a phenyl or a naphthyl.

The reaction can also be carried out by replacing the Ar or Ar' group with a vinyl group.

The catalysts of type 1, 2, 3 and 4 prove to be very effective for this heterogeneous catalysis reaction. They can be reused after reaction and reactivation by washing and drying. They can also be recycled by the plants according to the method described in the rhizofiltration section.

The reaction is general, including with non-activated halogenated, including chlorinated, derivatives. The nature of the heat treatment of the biomass slightly affects the catalytic activity; it is preferable to use a heat treatment in air. On the other hand, the acid treatment provides a very significant beneficial effect. Comparison of the results with Plos One 2014, 9, issue 1, e87192 (Parker et al) suggests this. The authors describe examples of the Suzuki reaction involving 12 mol % of palladium. If the Eco-Pd catalysts of type 1, 2, 3 and 4 have a catalytic activity, Eco-Pd$_{cat3}$ leads to very good yields starting from 0.0025% of Pd! This result is not only much superior to those of this article, but they are all examples described in the literature with non-biosourced catalytic systems.

The reaction is possible with the aryl chlorides, which are usually not very reactive, without the necessity to add tetrabutylammonium bromide (TBAB) conventionally described as useful for preventing the formation of aggregates of particles of Pd(0) responsible for a loss of catalytic activity. It appears that the polymetallic nature of the Eco-Pd avoids the formation of these aggregates which conventionally affect the catalytic activity. It is possible that the other cations present in the catalysts (cf. ICP MS analyses presented above) exercise a donor effect which promotes the oxidizing addition on the Pd by the formation of other complexes. This technical aspect is important, as the processes requiring additions of salts such as TBAB, NaCl, Na$_2$SO$_4$, etc. increase the quantity of waste formed, which leads to an additional treatment of the residual effluents. The Eco-Pds avoid this problem and lead to greener systems. In these difficult cases, Eco-Pd$_{cat3}$ is preferred to Eco-Pd$_{cat4}$. It is possible to add phosphines (such as PPh$_3$); a slight improvement in yields is observed.

A few typical examples with operating conditions are given in the table below:

| catalyst | X | Y | Z | [Pd] (mol %) | Additional compound | Base (eq) | T ° C./h | Yield % |
|---|---|---|---|---|---|---|---|---|
| Eco-Pd$_{cat3}$ | I | OMe | H | 0.05 | — | K$_3$PO$_4$ | 120/16 | 73 |
| Eco-Pd$_{cat3}$ directly recycled | I | OMe | H | 0.05 | — | K$_3$PO$_4$ | 120/16 | 62 |
| Eco-Pd$_{cat3}$ | I | OMe | H | 0.05 | 4 eq PPh$_3$ | K$_3$PO$_4$ | 120/16 | 80 |
| Eco-Pd$_{cat5}$ | I | OMe | H | 0.05 | — | K$_3$PO$_4$ | 120/16 | 68 |
| Eco-Pd$_{cat5}$ | I | OMe | H | 0.05 | 2 eq PPh$_3$ | K$_3$PO$_4$ | 120/16 | 70 |
| Eco-Pd$_{cat3}$ + Eco-Ni derivative of *Alyssum murale* | I | OMe | H | 0.05 | 1% Ni of Eco-Ni | K$_3$PO$_4$ | 120/16 | 99 |
| lageEco-Pd$_{cat3}$ | Br | (CO)Me | H | 0.05 | — | K$_3$PO$_4$ | 120/16 | 100 |
| Eco-Pd$_{cat4}$ | Br | (CO)Me | H | 0.05 | — | K$_3$PO$_4$ | 120/16 | 100 |
| Eco-Pd$_{cat3}$ | Br | (CO)Me | H | 0.0025 | — | K$_3$PO$_4$ | 120/16 | 73 |
| Eco-Pd$_{cat3}$ | Cl | H | H | 0.05 | — | K$_3$PO$_4$ | 120/7 | 57 |
| Eco-Pd$_{cat3}$ | Cl | H | H | 0.05 | 1% Ni of Eco-Ni | K$_3$PO$_4$ | 120/7 | 68 |
| Eco-Pd$_{cat3}$ | Cl | CN | H | 0.10 | — | K$_3$PO$_4$ | 120/16 | 76 |
| Eco-Pd$_{cat4}$ | Cl | CN | H | 0.10 | — | K$_3$PO$_4$ | 120/16 | 15 |
| Eco-Pd$_{cat3}$ | Cl | NO$_2$ | H | 0.10 | — | K$_3$PO$_4$ | 120/16 | 63 |
| Eco-Pd$_{cat4}$ | Cl | NO$_2$ | H | 0.10 | — | K$_3$PO$_4$ | 120/16 | <10 |

3) π-Allylic Complex Chemistry

The reactivity of the π-allylic complexes is illustrated by the nucleophilic addition of an enamine on a π-allylic complex.

Preparation of the Complex:

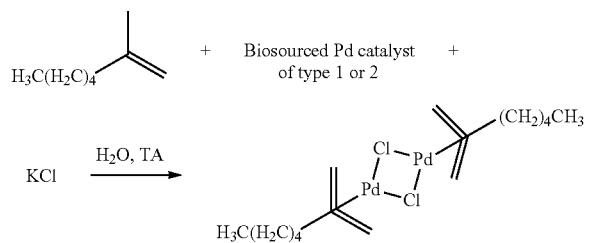

Reaction of the Complex with a Nucleophile:

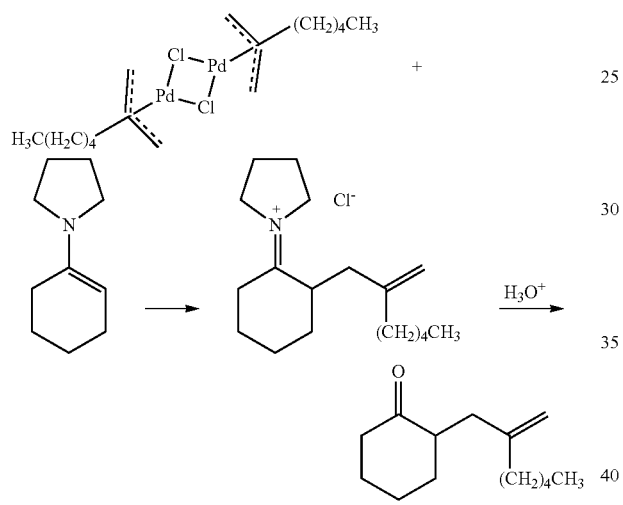

4) Arylation and Alkenylation of C, N, O, S, P and Se Nucleophiles (Buchwald-Hartwig Type Reactions)

The Buchwald-Hartwig reaction has been illustrated in a cyanation version, based on the use of copper thiocyanate (I) instead of the highly toxic cyanides conventionally used.

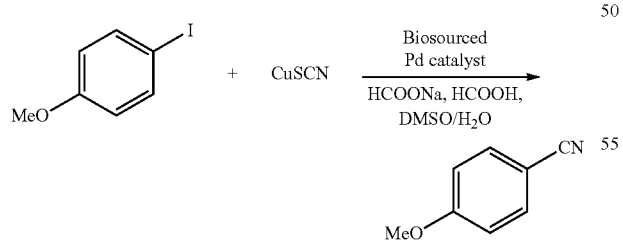

5) Carbonylation and Ene-Reaction

The insertion of a carbonyl unit is possible: it constitutes a good access route to the carboxylic esters. The biosourced Pd catalysts are also used for the ene-reactions.

The biosourced Pd catalysts can also catalyze these two reaction families from one and the same substrate.

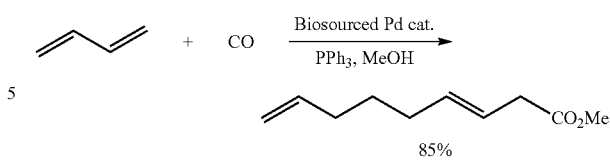

Pd(II) Chemistry

1) Wacker-Tsuji Oxidation

The Wacker-Tsuji oxidation reaction allows the production of ketones from alkenes in a method of industrial importance (industrial synthesis of ethanal from ethene). The catalysts based on biosourced Pd efficiently catalyze the reaction and can be easily recycled when they are supported (in particular for the catalyst of type 3).

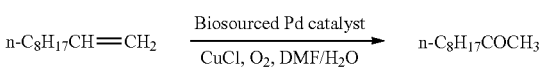

2) Oxidation of Alcohols

The controlled oxidation of a primary alcohol to aldehyde by dioxygen is quantitative when it is catalyzed by biosourced Pd catalysts.

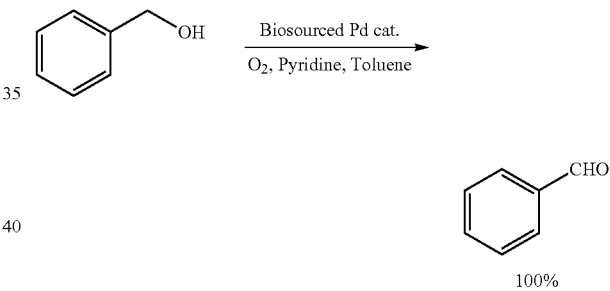

3) Reaction of Alkenes or Alkynes with Oxygen-Containing, Nitrogen-Containing or Carbon-Containing Nucleophiles The nucleophiles such as alcohols or amines are capable of adding onto a double or triple bond by catalysis with biosourced Pd of type 2 or 3, the chemoselectivity being able to be different depending on the type of catalyst used. It is a good access route to the heterocycles.

4) Oxidizing Coupling of Aromatic Compounds

This reaction works particularly well starting from the acetates of platinoids. They can be formed in situ starting from the sodium chloride and acetate form:

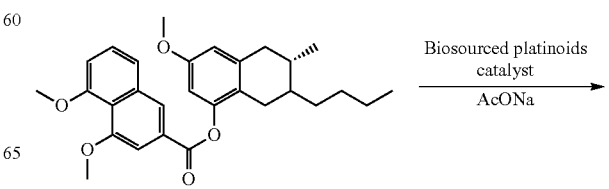

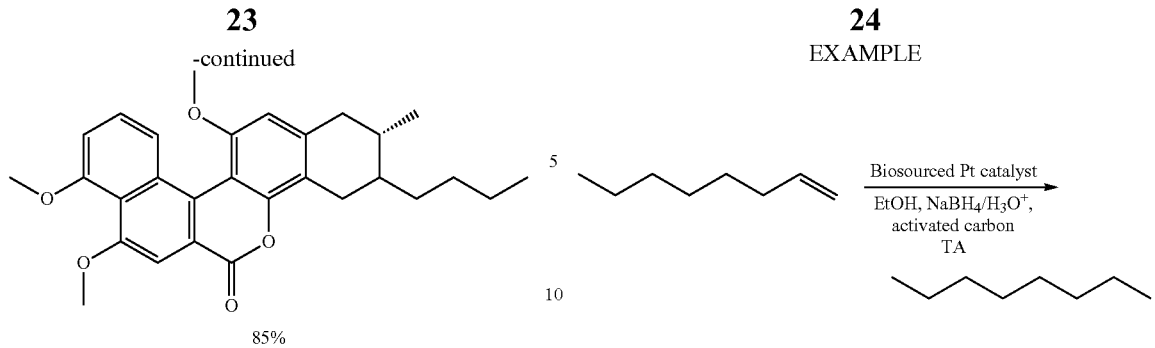

85%

5) Regioselective Reactions Based on Chelation and the Involvement of Heteroatoms The coupling between an alkene and an aromatic derivative is a possible reaction; its regioselectivity can be controlled by intramolecular chelation.

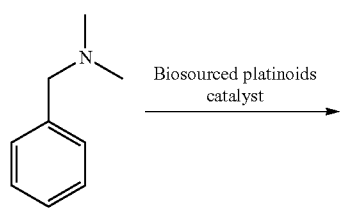

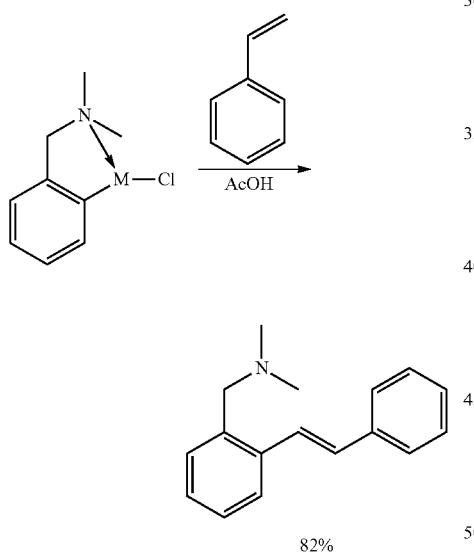

82%

6) Cyclopropanation of Alkenes Using Diazo Compounds

The functionalized cyclopropanes, units present in numerous molecules of industrial interest, can be obtained from alkenes and diazo reagents catalyzed with biosourced Pd.

Bio-Sourced Platinum Chemistry

1) One-Pot Reduction of Olefins and Nitrated Compounds (Reference Example with a Hydride):

The catalyst actively reacts to the hydrolysis of the sodium borohydrides by hydrochloric acid which releases hydrogen. This hydrogen generated in situ reduces the double bonds by adsorption on the Pt(0). The triple bonds are also involved in the reaction. Lowering the temperature of the reactions to −25° C. starting from the same arrangement considerably increases the selectivities of the catalysis.

EXAMPLE

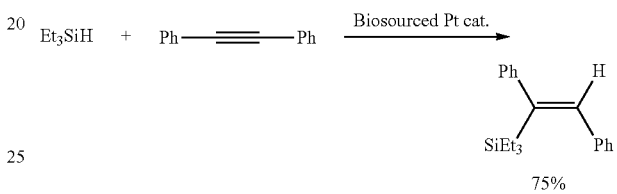

2) Hydrosilylation of Olefins and Alkynes

The hydrosilylation of unsaturated compounds is a reaction commonly used in the silicon industry which can be catalyzed by the biosourced Pt catalysts.

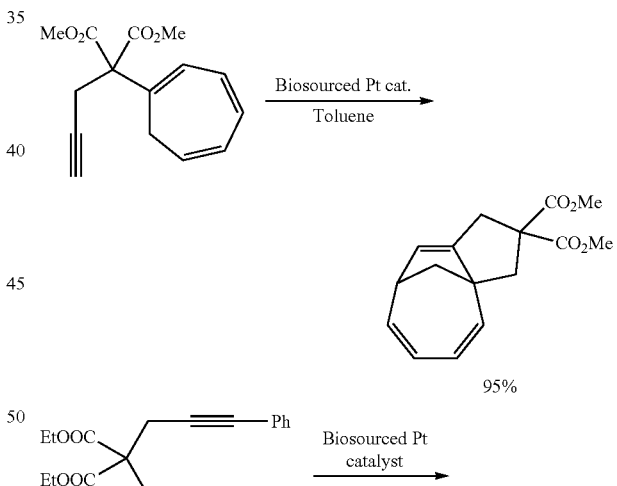

75%

3) Cycloadditions

The metathesis and cycloisomerization of enynes are two examples of cycloaddition efficiently catalyzed by the biosourced Pt catalysts.

95%

70%

4) Cascade Reactions

The biosourced Pt catalysts make it possible to carry out the cascade carbocyclization of polyunsaturated compounds.

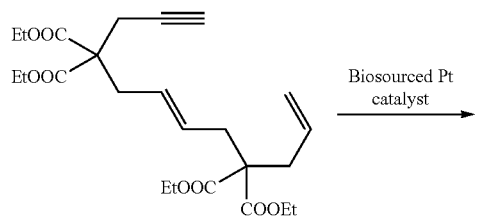

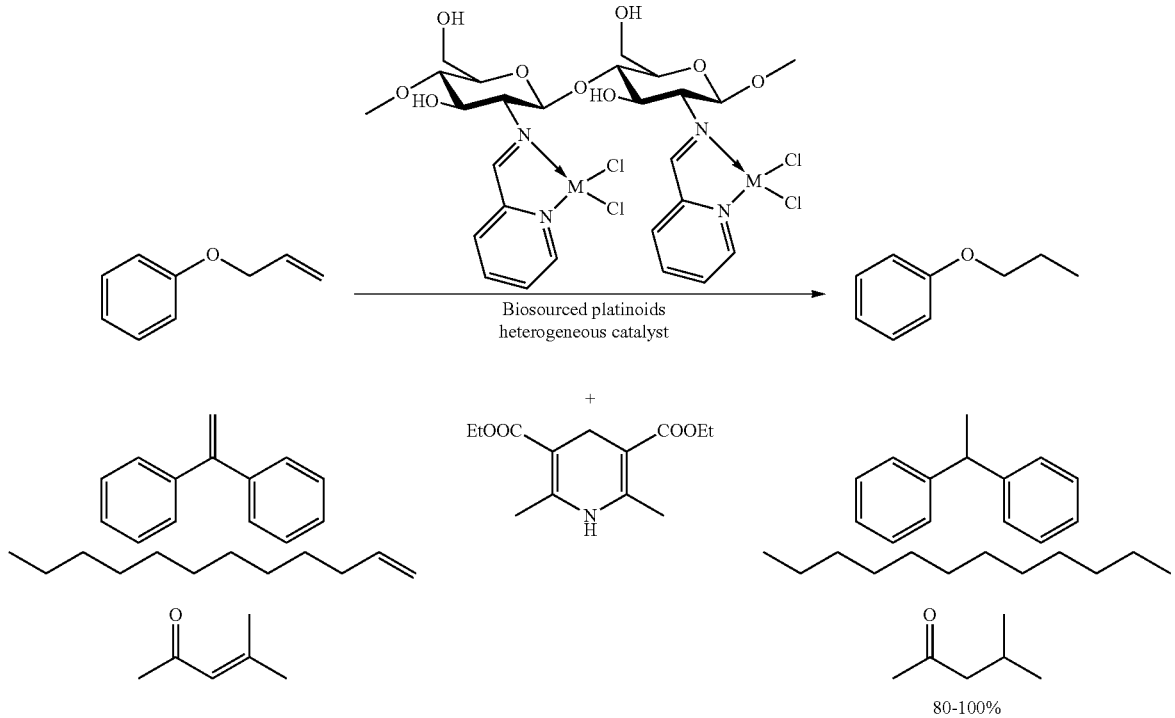

b) Reduction of Double-Bonds in the Presence of a Hydride Donor:

The reaction is carried out with a hydride donor which is simple to produce (by Hantzsch reaction) and without any handling risk. The reaction works as efficiently on the electron-rich alkenes as on unenriched unsaturated derivatives. The use of an insoluble ligand (chitosan-pyridyl) makes it possible to reuse the catalyst at the end of the reaction by simple filtration:

-continued

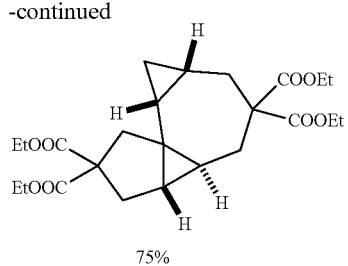

75%

Bio-Sourced Rhodium Chemistry

1) Catalytic Hydrogenation a) Example of Hydrogenation Reaction (Reference Example with Hydrogen):

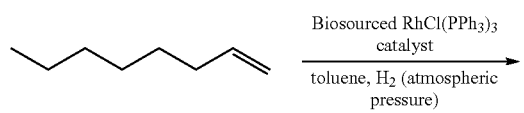

2) Allylic Isomerization

The isomerization reactions catalyzed by the biosourced Rh catalysts constitute a good access route to enol ethers or enamines.

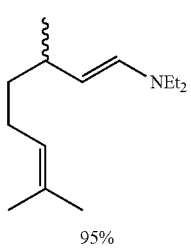

95%

3) Cycloaddition

Cycloadditions such as the cyclotrimerization [4+2+2] of an enyne with 1,3-butadiene can be facilitated by biosourced Rh catalysis.

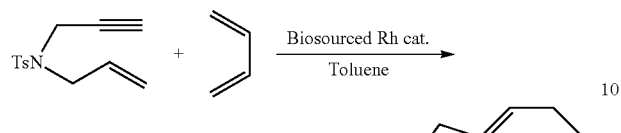

90%

Other cyclization reactions such as the ene-reactions and the cycloisomerizations of dienes or enynes are also possible.

4) Ene-Reaction

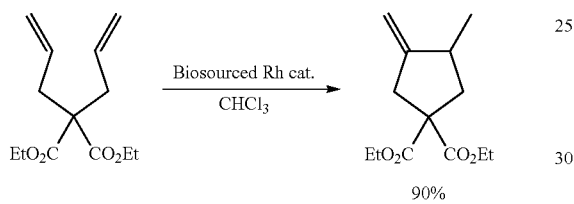

90%

5) Cycloisomerization

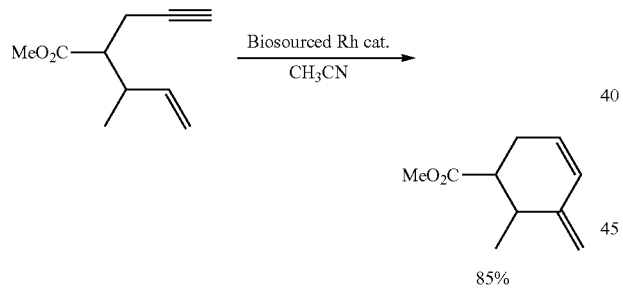

85%

6) Hydroboration

The regioselective preparation of an alcohol by hydroboration of an alkene using biosourced Rh catalysts is a very efficient reaction.

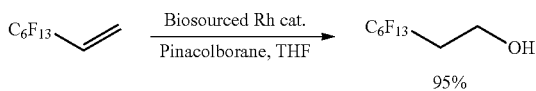

95%

III—Green Reductions

The Eco-Pd$_{cat1,2,3,4,5,6,8}$ ecocatalysts have useful reducing properties which have been tested successfully on three reactions models, the reduction of nitrated derivatives to amine (1) and the selective reduction of citral to citronellal (2).

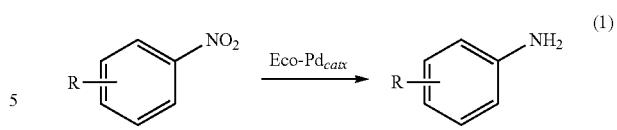 (1)

R=alkyl, aryl, heteroatom

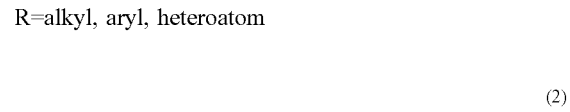 (2)

(3)

The active ecocatalysts in these three reactions are given in the table below:

| Nature of the catalyst | Pd level (ICP MS) | XPS data | Activation of the catalyst | Conditions |
|---|---|---|---|---|
| Eco-Pd$_{cat1}$ | 7.80% | Pd(0) | Thermal at 800° C. under CO$_2$ | HCOONH$_4$/ MeOH/reflux |
| Eco-Pd$_{cat2}$ | 1.53% | Pd(0) + PdO | Thermal at 800° C. under argon | HCOONH$_4$/ MeOH/reflux |
| EcO-Pd$_{cat7}$ | 9.10% | Pd(0) + traces of Pd(II) | Thermal at 600° C. under CO$_2$ | HCOOH/ Et$_3$N/reflux |
| Eco-Pd$_{cat8}$ | 2.58% | Pd(0) | Thermal at 600° C. under argon | HCOOH/ Et$_3$N/reflux |
| EcO-Pd$_{cat9}$ | 9.20% | Pd(0) | — | HCOOH/ Et$_3$N |

EXPERIMENTAL SECTION

Bio-Sourced Palladium Chemistry

Example 1: Pd(0) Chemistry

Example 1.1: Reaction of Aryl Halides with Alkenes or Aromatics (Heck Reaction)

Typical Experimental Protocol:

1 mg of catalyst of type 3 (i.e. 1.17×10$^{-4}$ mmol of Pd) in 2 mL of N-methyl 2-methyl pyrrolidone is placed in a single-necked reaction vessel. After being placed under a nitrogen atmosphere, 6×10$^{-2}$ mmole (19.3 mg) of TBAB, 0.13 mmole (10.7 mg) of sodium acetate, 0.10 mmole (11.2 µl) of iodobenzene and 0.16 mmole (16 µl) of styrene are added. The reaction mixture is heated at 140° C. for 24 h under nitrogen. After cooling, 5 mL of cyclohexane and 5 mL of water are added to the mixture. After decantation, the organic phase is washed with water (5×5 mL). The organic phases are combined, dried over MgSO$_4$, filtered and concentrated under vacuum. The crude product is easily purified by chromatography if necessary. The aqueous phase is stored in order to be treated and recycled by rhizofiltration using the metallophytes described.

By using an insoluble support of natural origin, chitosan, and by suitably derivatizing it, it is possible to form a polymer liganded to the platinoids, which allows coupling reactions to be carried out in heterogeneous phase:

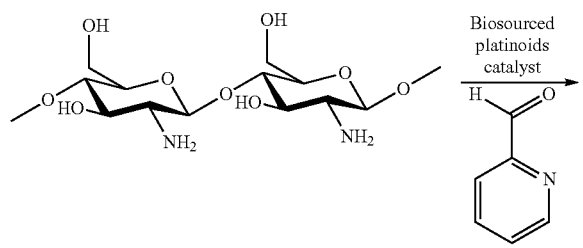

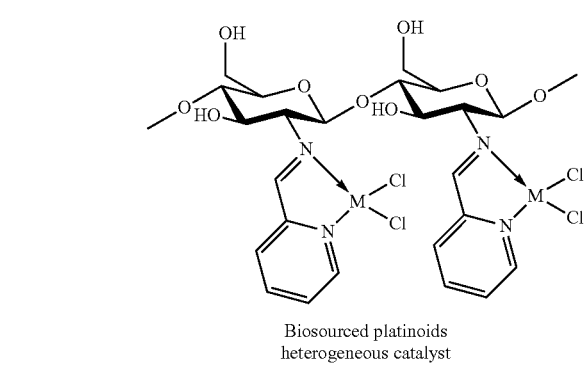

Biosourced platinoids heterogeneous catalyst

This catalyst can thus be recovered by simple filtration and reused. Its efficiency is maintained in the Heck reaction:

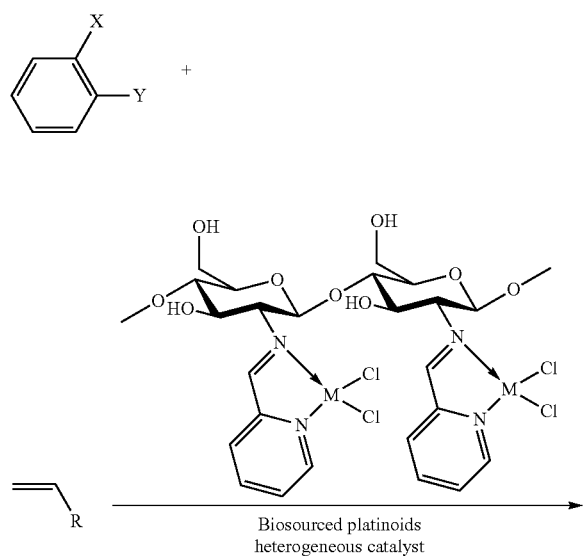

Biosourced platinoids heterogeneous catalyst

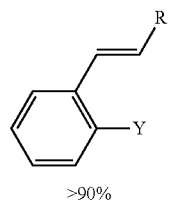

X = Br, I
Y = H, OMe
R = Ph, COOMe

>90%

Example 1.2: Reaction of Arylic Coupling with Organometallic Compounds, an Example of a Typical Suzuki Reaction 5 mL of toluene, 4-bromoacetophenone (1.0 mmol), phenylboronic acid (1.2 mmol), $K_3PO_4$ (3.0 mmol) and the Eco-Pd$_{cat4}$ catalyst (quantity corresponding to 0.05% mol of Pd according to ICP-MS analyses) are introduced into a Schlenk tube under a stream of dinitrogen. The mixture is heated under stirring at 120° C. The progress of the reaction is monitored by regular samples analyzed by GC-MS, the yield reaching 100% in 16 h.

In the case of substrates which are not very reactive, the addition of 1 mol % of Eco-Ni(PPh$_3$)$_3$ leads to a significant improvement in the yield of the reaction, this yield being greater than that obtained with the biosourced Eco-Pd or Eco-Ni (PPh$_3$)$_3$ catalysts alone, separately.

Example 1.3: Chemistry of the π-Allylic Complexes

The reactivity of the π-allylic complexes is illustrated by the nucleophilic addition of an enamine to an π-allylic complex.

Preparation of the Iso-Octene Derivative Complex 1 mL of distilled water, degassed by bubbling through $N_2$, a quantity of catalyst of type 2 or 3 corresponding to 1 equivalent of Pd according to ICP-MS assays as well as potassium chloride (2 equivalents) are introduced into a 5 mL flask. The solution is stirred at AT for 1 h then 3 equivalents of 2-methylheptene are added. The mixture is stirred at AT for 20 h. The reaction medium is extracted with dichloromethane, dried over $MgSO_4$, then evaporated, leading to the desired complex without additional purification.

Reaction of the Complex with a Nucleophile, 1-Pyrrilidino-1-Cylohexene:

47 mg (0.088 mmol) of the previous complex are dissolved in a mixture of DMSO/ethanol (1.5 mL/1.0 mL) in a sealed tube equipped with a magnetic stirrer, then 42 mg (0.28 mmol) of 1-pyrrilidino-1-cyclohexene is added. The mixture is heated at 100° C. in an oil bath until the reaction is complete (monitoring by TLC). After the addition of a 1 M solution of dilute hydrochloric acid, the reaction medium is extracted with dichloromethane, the organic phase is dried over $MgSO_4$, evaporated then purified by chromatography on silica gel, in order to produce the final product with a yield of 38%.

Example 1.4: Arylation and Alkenylation of C, N, O, S, P and Se Nucleophiles (Buchwald-Hartwig Type Reactions): the Cyanation of 4-Iodioanisole CuSCN (1 equivalent), iodoanisole (1.25 equivalents), biosourced Pd catalyst of type 3 (preferably, but the catalysts of type 2, 4 and 5 also catalyze the reaction to a lesser extent) (0.01 equivalent), HCOONa (3 equivalents), HCOOH (0.1 equivalent) as well as a DMSO/water mixture (8/1) (3 mL) are introduced into a sealed tube. The mixture is heated in an oil bath at 100° C. for 36 h, the duration necessary for completion of the reaction according to samples taken for GC-MS analysis. The yield reaches 62%.

Example 2: Pd(II) Chemistry

Example 2.1: Wacker-Tsuji Oxidation: Oxidation of Decene

Catalyst of type 2 or 4 (0.1 equivalent Pd), CuCl (1 equivalent) and a DMSO/water mixture (7/1) are introduced into a flask equipped with a magnetic stirrer. The mixture is supplied with dioxygen via a balloon punctured through a septum capping the reaction apparatus. The mixture is stirred vigorously to allow enrichment of the solution with $O_2$, at AT. After stirring for one hour, 1-decene (1 equivalent) is introduced dropwise, over 10 minutes. The medium is stirred for 24 h at AT, under a dioxygen atmosphere. GC-MS analyses indicate a dodecanone yield of 70%.

Example 3: Reference with a Hydride: Bio-Sourced Platinum Chemistry

One-Pot Reduction of Olefins and Nitrated Compounds
Example Reduction of Octene
1 g of finely reduced activated carbon, 40 mL of anhydrous ethanol, 1 mL of a 0.2 M solution of biosourced Pt catalyst of type 1 are introduced into a flask equipped with a septum and a magnetic stirrer. 5 mL of an 1.0 M ethanolic solution of $NaBH_4$ are then introduced, then after stirring for one minute, 4 mL of a 6 M solution of hydrochloric acid is injected, for the in situ formation of dihydrogen. 6.3 mL (40 mmoles) of 1-octene are then added to the syringe, dropwise. Hydrogenation is complete in 30 minutes.

Example 4: Bio-Sourced Rhodium Chemistry

Bio-Sourced Rhodium Chemistry
Allylic Isomerization of Neryldiethylamine to Enamine
1 mmol of neryldiethylamine is diluted in 6 ml of anhydrous THF in a pressure-resistant single-necked flask under an inert atmosphere. The biosourced rhodium complex is added (1 mol % Rh). The mixture is heated at 110° C. in order to produce the crude enamine in a quantitative fashion. The solvent is eliminated under reduced pressure and the enamine is rapidly chromatographed.

Example 5: Characterization of the Catalysts

The Lewis Acid Properties
The preparation of a catalyst originating from ashes derived from roots rich in PGE (platinoids group) and treated with HCl is innovative. The Lewis acid properties were determined by the sorption/desorption technique with pyridine and study by IR spectroscopy. The results presented hereafter relate to Eco-Pd$_{cat3}$ and Eco-Pd$_{cat4}$.

Eco-Pdcat$_4$
Vibration bands at 1442 cm$^{-1}$ and between 1599 and 1624 cm$^{-1}$ reflect the Lewis acidity of the catalyst. Several types of Lewis acid sites are demonstrated. The Lewis acidity is different from that observed with commercial PdCl$_2$: the signals around 1600 cm$^{-1}$ have a higher frequency than in the case of PdCl$_2$, which suggests that certain Lewis acid sites are stronger than in the case of PdCl$_2$.

A band at 1526 cm$^{-1}$ corresponds to Brösted acidity, which was absent with PdCl$_2$.

Eco-Pd$_{cat3}$
The signals at 1448 and 1606 cm$^{-1}$ correspond to Lewis acidity, close to PdCl$_2$.
A signal located at 1527 cm$^{-1}$ is weak, and therefore difficult to compare to Brösted acidity. The signal at 1636 cm$^{-1}$ may be due to a stronger Lewis acidity.

It is noted that the Lewis acidity of this catalyst is closer to the Lewis acidity of PdCl$_2$.

Conclusion
Eco-Pd$_{cat4}$ and Eco-Pd$_{cat3}$ have a different and complementary acidity. Eco-Pd$_{cat4}$ is clearly distinguished from commercial PdCl$_2$.

Example 6: Green Reductions

General operating method: 97% formic acid is added to a mixture of substrate, activated Eco-Pd ecocatalyst and triethylamine at ambient temperature. The solution is taken to reflux and monitored by GC MS until the substrate disappears or the reaction does not progress. The catalyst is removed by filtration and the residue is washed with ethyl acetate. The organic phases are combined, dried over magnesium sulphate, filtered and concentrated.

Example 7: Characterization of the Degrees of Oxidation by XPS in the Different Catalysts All the catalysts prepared were analyzed by XPS. Heat treatment of the roots is more difficult than that of foliar systems. Thus, irrespective of the conditions implemented, C, N, S and P are present on contact with the metallic materials. Sulphur is particularly present in the ashes and catalysts which derive from the Brassicaceae, such as *Brassica juncea* and *Sinapis alba*. The phosphorus originates from numerous phosphorylated metabolites of the plants. It is present in the form of phosphates does not therefore constitute a poison for the catalysts.

Significant differences are observed between the materials prepared.

The analyses are carried out with the ESCALAB 250 device from Thermo Electron. The excitation source is the monochromatic source, Al Kα (1486.6 eV). The surface analyzed has a diameter of 400 μm. The spectra of the photoelectrons are calibrated by binding energy with respect to the energy of the C—C component of the Carbon C1s at 284.8 eV. The powder is dispersed over graphite adhesive tape.

The quantification step consists of counting the electrons emitted by the different constituents of the material. Without the use of reference samples, all of the electrons collected are considered as representing 100% of the constituents of the sample. This is therefore a semi-quantification method.

Moreover, in order to take account of the different radiation/matter and electron/matter interaction phenomena, corrective factors (Scofield coefficients) are applied to this number of electrons collected. The atomic percentages for each of the constituents are obtained.

Thus in the case of EcoPdcat2, the following are the main elements found:

| Name | Peak BE | FWHM eV | Area (P) CPS.eV | At. % | Q |
|------|---------|---------|-----------------|-------|---|
| Cl2p | 199.26 | 1.82 | 2370.18 | 2.62 | 1 |
| C1s | 284.88 | 1.86 | 29317.11 | 74.55 | 1 |
| Pd3d | 335.63 | 1.09 | 3057.57 | 0.49 | 1 |
| Ca2p | 347.40 | 1.45 | 1836.65 | 0.93 | 1 |
| O1s | 533.03 | 4.14 | 20105.61 | 17.97 | 1 |
| Na1s | 1072.23 | 1.50 | 9269.86 | 3.44 | 1 |

FIG. 3: Pd3d and Ca2p scan

| Name | Peak BE | FWHM eV | Area (P) CPS.eV | At. % | Q |
|------|---------|---------|-----------------|-------|---|
| Pd3d5 A | 335.67 | 1.17 | 1641.89 | 100.00 | 1 |
| Pd3d3 A | 340.95 | 1.17 | 1136.16 | 0.00 | 0 |

The presence of a lot of carbon is noted, which is normal during mild calcination of roots. There is also oxygen and a little chlorine (softened water for the roots) and sodium.

The palladium peaks have been deconvoluted. A single species is present for palladium, which indicates that only 1 degree of oxidation of palladium is present. According to the literature, the component 3d5/2 with a binding energy of 335.67 eV corresponds to palladium(0). It can therefore be concluded that Eco-Pd$_{cat2}$ contains only metallic palladium.

This Result is to be Noted and Compared with the Recent Publication:

Plos One 2014, 9, issue 1, e87192 (Parker et al). The authors describe the use of a laboratory plant model, undergoing hydroponic cultivation using a solution of potassium tetrachloropalladate. The methods and objectives are therefore very different. The ecological aspects are not taken into account: the nature of the plant (a laboratory plant which is not suited to the problem), the Pd salts ($K_2PdCl_4$ instead of nitrated salts originating from organic chemistry reactions), the biological knowledge (biological rhythm, the growth capacity of the root system, plant dynamics, bioaccumulation capacity and recycling objectives) are not taken into account. The results of the XPS analyses lead to a Pd(II)/Pd(0) mixture, which reflects the benefit of our approach. This benefit is reinforced by the superiority of the Eco-Pd catalysts in organic synthesis.

The XPS analyses of the other catalysts lead to the following conclusions:

| Name of the catalyst | Heat treatment | Acid treatment | Pd(0) | Pd(II) |
|------|------|------|------|------|
| Eco-Pd$_{cat1}$ | In air | — | Pd(0) | PdO |
| Eco-Pd$_{cat2}$ | Under argon | — | Pd(0) | — |
| Eco-Pd$_{cat3}$ | In air | HCl | — | PdCl$_x$, PdO, |
| Eco-Pd$_{cat4}$ | Under argon | HCl | Of the traces | PdCl$_X$ and PdO |
| Eco-Pd$_{cat7}$ | In air | HCOOH | Pd(0) | Traces of Pd(II) |
| Eco-Pd$_{cat8}$ | Under argon | HCOOH | Pd(0) | Traces of Pd(II) |

The invention claimed is:

1. A method of performing organic synthesis reactions utilizing a composition as a catalyst, the composition comprising a metal catalyst originating after acid treatment of ashes obtained after heat treatment of a plant or part of a plant belonging to one of the genera selected from the group consisting of green arrow arum or *Peltandra virginica*, cucumber or *Cucumis sativus*, garden cress or *Lepidium sativum*, Canadian pondweed or *Elodea canadensis*, spinach or *Spinacia oleracea*, water hyacinth or *Eichhornia crassipes*, alfalfa or *Medicago sativa*, maize or *Zea mays*, white mustard or *Sinapis alba*, brown mustard or *Brassica juncea*, barley or *Hordeum vulgare*, nettle or *Urtica dioica*, lacy phacelia or *Phacelia tanacetifolia*, radish or *Raphanus sativus*, perennial rye-grass or *Lolium perenne*, Italian rye-grass or *Lolium multiflorum*, hooked bristlegrass or *Setaria verticillata* and tobacco or *Nicotiana tabacum*,
said plant having accumulated at least one of the platinoids selected from the group consisting of platinum, palladium, osmium, iridium, ruthenium, and rhodium, the metal catalyst comprising metal or metals of which are selected from the group consisting of the metals originating from said plant, and the metal or metals of which present in the composition originate exclusively from the plant before calcination.

2. The method according to claim 1, wherein the heat treatment of a plant or part of a plant is carried out in air.

3. The method according to claim 1, wherein the heat treatment of a plant or part of a plant is carried out under an inert gas atmosphere.

4. The method according to claim 1, wherein the acid treatment is carried out with an acid selected from the group consisting of hydrochloric acid, sulphuric acid, trifluoromethanesulphonic acid, nitric acid, perchloric acid, phosphoric acid, trifluoroacetic acid, para-toluene sulphonic acid, acetic acid, formic acid, oxalic acid, and mixtures thereof.

5. The method according to claim 1, wherein the aqueous phase of the reaction mixture obtained after use as a catalyst of the compositions containing a metal catalyst originating after acid treatment of the ashes obtained after heat treatment of a plant or part of plant is recycled by rhizofiltration using said plants.

6. The method according to claim 1 for the implementation of the organic synthesis reactions of functional conversions by catalysis selected from the group consisting of reactions of formation of carbon-carbon, a Heck reaction, a Sonogashira reaction, nucleophilic addition reactions of an enamine on pi-allylic complexes, Buchwald-Hartwig reactions, carbonylation reactions and ene-reactions, a Wacker-Tsuji oxidation, oxidation of alcohols, a reduction of olefins and of nitrated compounds and nitriles, a hydrosilylation of olefins and of alkynes, and an allylic isomerization.

7. The method according to claim 1 for the implementation of organic synthesis reactions of functional conversions by catalysis selected from the group consisting of a Suzuki reaction, a Heck reaction, a Sonogashira reaction, and a reduction of olefins and of nitrated compounds and nitriles.

8. The method according to claim 1, wherein the amount of the metallic or polymetallic catalyst contained in the composition is used in very low doses of 0.001 mol % to 0.15 mol %.

9. The method according to claim 1, wherein in the composition containing at least one mono- or polymetallic agent used in the implementation of the organic synthesis reactions of functional conversions by catalysis, the concentration of metal is comprised between 600 and 120,000 mg·kg$^{-1}$ in the case of platinum, between 5,000 and 180,000 mg·kg$^{-1}$ in the case of palladium and between 30 and 22,000 mg·kg$^{-1}$ in the case of rhodium.

10. The method according to claim 1, wherein the plant or part of a plant belongs to one of the genera selected from the group consisting of white mustard or *Sinapis alba*, brown mustard or *Brassica juncea*, and Italian rye-grass or *Lolium multiflorum*.

11. The method according to claim 1, wherein the plant has accumulated at least one of the platinoids selected from the group consisting of platinum, palladium, and rhodium.

12. The method according to claim 4, wherein the acid treatment is carried out with a hydrochloric acid-nitric acid mixture or an acetic acid-nitric acid mixture.

13. The method according to claim 8, wherein the metallic or polymetallic catalyst contained in the composition comprises between 0.0025 mol % and 0.15 mol % Pd.

* * * * *